United States Patent [19]
Tsukamura et al.

[11] Patent Number: 5,184,359
[45] Date of Patent: Feb. 9, 1993

[54] STOOL-TYPE APPARATUS FOR SAMPLING AND ASSAY OF URINE WITH SWINGABLE CARRIAGE

[75] Inventors: Naoki Tsukamura; Kiyoshi Alyfuku; Yuzuru Nakamura; Yoshiki Hiruta; Hiroshi Tsuboi, all of Fukuoka, Japan

[73] Assignee: Toto Ltd., Kita-kyushu, Japan

[21] Appl. No.: 748,211

[22] Filed: Aug. 22, 1991

[30] Foreign Application Priority Data

| Aug. 24, 1990 | [JP] | Japan | 2-223324 |
|---|---|---|---|
| Sep. 4, 1990 | [JP] | Japan | 2-233740 |
| Sep. 4, 1990 | [JP] | Japan | 2-233741 |
| Sep. 4, 1990 | [JP] | Japan | 2-233742 |
| Oct. 23, 1990 | [JP] | Japan | 2-285367 |
| Oct. 23, 1990 | [JP] | Japan | 2-285368 |
| Oct. 25, 1990 | [JP] | Japan | 2-287624 |
| Oct. 26, 1990 | [JP] | Japan | 2-290304 |
| Nov. 22, 1990 | [JP] | Japan | 2-318834 |
| Nov. 22, 1990 | [JP] | Japan | 2-318835 |
| Nov. 22, 1990 | [JP] | Japan | 2-318836 |
| Nov. 26, 1990 | [JP] | Japan | 2-324668 |
| Nov. 26, 1990 | [JP] | Japan | 2-324670 |
| Nov. 26, 1990 | [JP] | Japan | 2-324671 |
| Nov. 26, 1990 | [JP] | Japan | 2-324672 |
| Nov. 26, 1990 | [JP] | Japan | 2-324673 |
| Nov. 26, 1990 | [JP] | Japan | 2-324674 |
| Nov. 26, 1990 | [JP] | Japan | 2-324675 |
| Nov. 26, 1990 | [JP] | Japan | 2-324676 |
| Nov. 26, 1990 | [JP] | Japan | 2-324677 |

[51] Int. Cl.$^5$ ............ E03D 11/00; A61B 5/00
[52] U.S. Cl. .................... 4/661; 4/420; 4/314; 128/760
[58] Field of Search .......... 4/31.4, 420, 301, 661; 128/632, 677, 736, 760, 771; 73/864.81–864.85

[56] References Cited

U.S. PATENT DOCUMENTS

| 4,636,474 | 1/1987 | Ogura et al. . |
|---|---|---|
| 4,961,431 | 10/1990 | Ikenaga et al. . |
| 4,962,550 | 10/1990 | Ikenaga et al. . |
| 4,982,741 | 1/1991 | Saito et al. ............ 128/771 |
| 5,073,500 | 12/1991 | Saito et al. ............ 128/760 X |
| 5,111,539 | 5/1992 | Hiruta et al. ............ 4/661 |

FOREIGN PATENT DOCUMENTS

| 292311 | 11/1988 | European Pat. Off. . |
|---|---|---|
| 57-59168 | 9/1980 | Japan . |
| 59-183969 | 4/1983 | Japan . |
| 59-217844 | 5/1983 | Japan . |
| 60-233551 | 5/1984 | Japan . |
| 60-117157 | 6/1985 | Japan . |
| 60-155977 | 8/1985 | Japan . |
| J6-3021555A | 7/1986 | Japan . |
| 987517 | 3/1965 | United Kingdom . |

Primary Examiner—Charles E. Phillips
Attorney, Agent, or Firm—Lowe, Price, LeBlanc & Becker

[57] ABSTRACT

A toilet system (10) with urine assay function is disclosed which comprises a toilet stool (12) having a toilet bowl (14) and a small urine-sampling cavity (52). A frame (42) is mounted on the toilet stool to support a testing sheet handling and transfer mechanism (30) which comprises a swingable carriage (46) and a slidable arm (50) supported by the carriage for linear telescoping movement. The carriage is swingable about a vertical axis (48) between a first position in which the carriage is oriented toward the sampling cavity and a second position in which the carriage is oriented to a lateral side of the stool wherein a disposal station is provided.

The toilet system enables the use of testing sheets (32) which are made from water insoluble materials.

Various other embodiments are also disclosed.

The system provides a high degree of reliability of analysis.

51 Claims, 38 Drawing Sheets

FIG.11
FIG.12
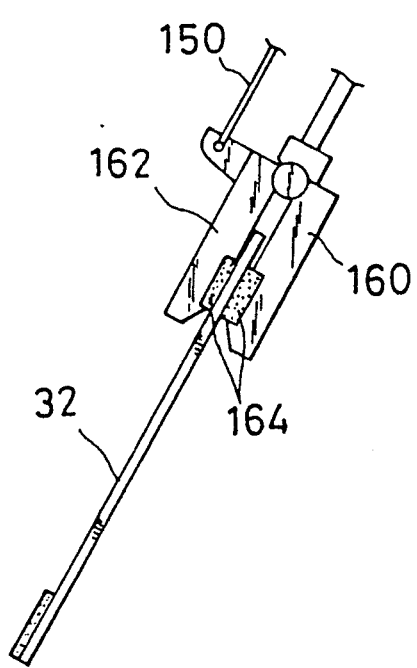
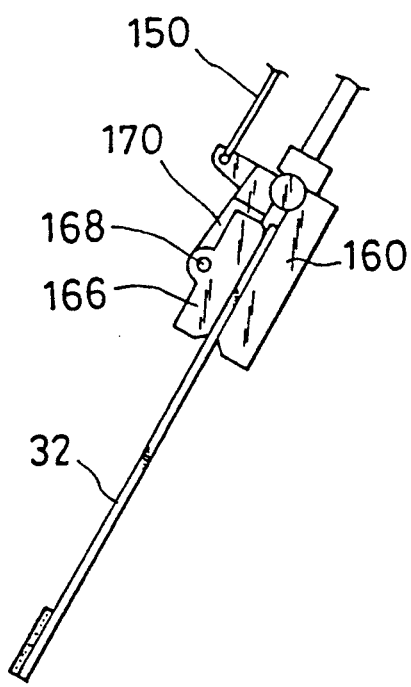

*FIG.15* *FIG.16*
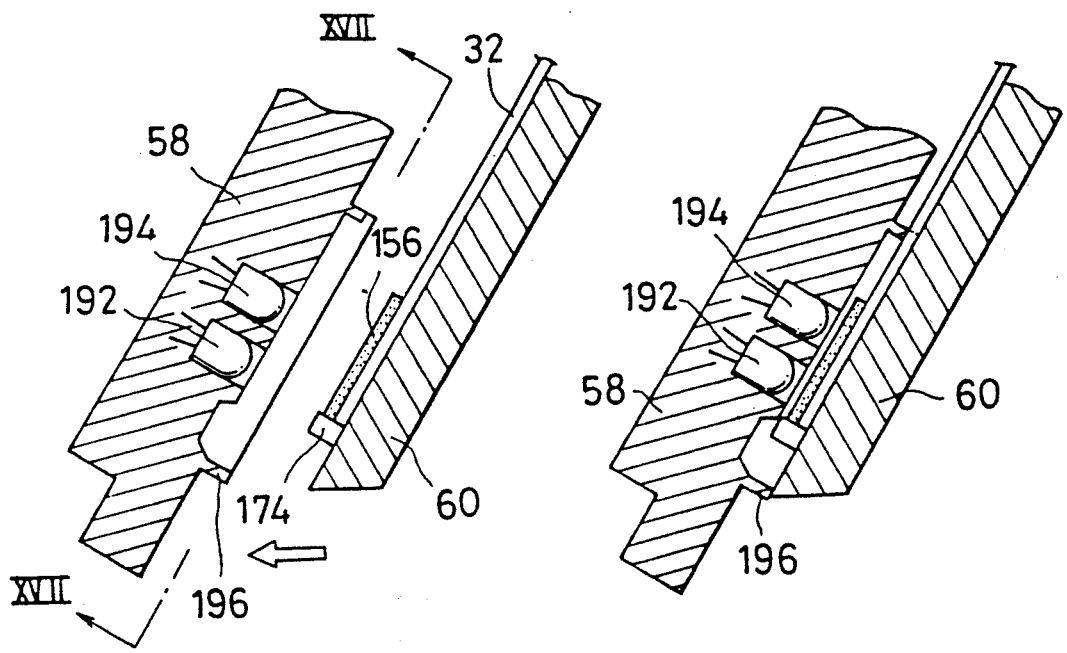
*FIG.17*
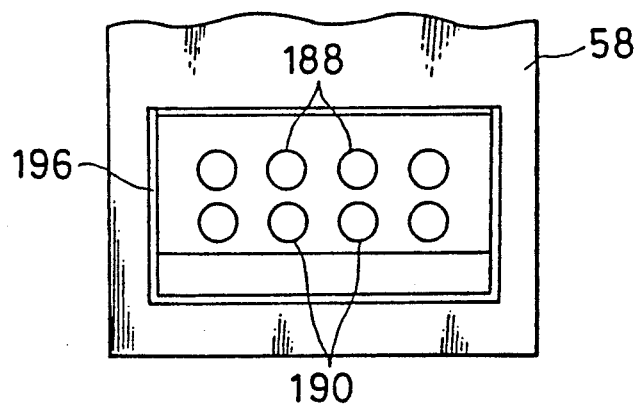

FIG./8G 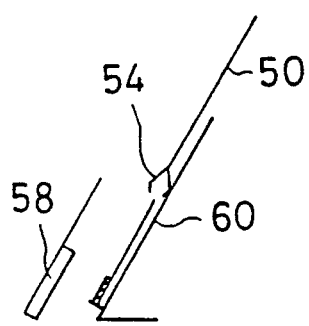 FIG./8H 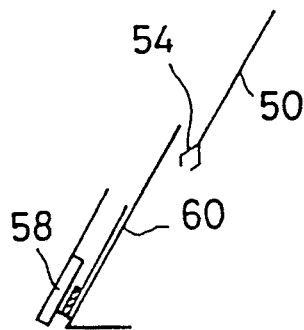 FIG./8I 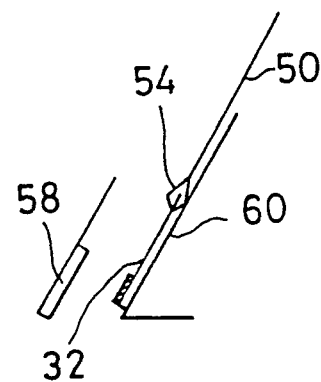
FIG./8J 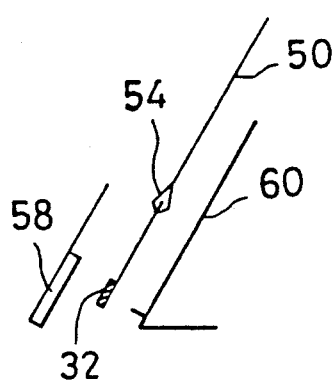 FIG./8K 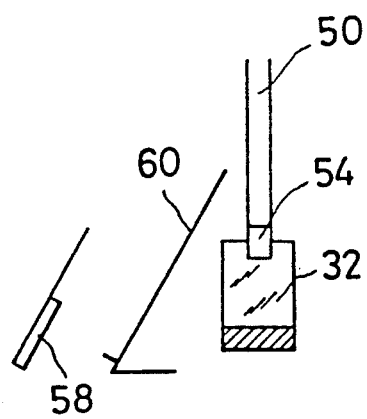

STOOL-TYPE APPARATUS FOR SAMPLING AND ASSAY OF URINE WITH SWINGABLE CARRIAGE

BACKGROUND OF THE INVENTION

1. Field of the Invention

The present invention relates generally to the art of assay of biological excrements. More specifically, the present invention relates to a toilet system having functions of sampling and assay of biological excrement such as urine. The present invention relates also to a testing sheet handling device suitable for use in a toilet system of the type mentioned as a sub-assembly therefor.

2. Description of the Prior Art

Biological excrements released from a human body provides an ideal source of information concerning the health conditions of individuals. For example, urine contains biological substances, such as glucose, albumin, urobilinogen and occult blood, the quantitative determination of which is helpful in the diagnosis of sickness such as diabetes.

Sampling of urine for the purposes of urinalysis is often cumbersome and unhygienic for individuals as well as for those engaged in the assay. Furthermore, there has been a need for an analyzing equipment which may be conveniently used at home for daily health check.

Accordingly, various toilet systems have been proposed which are provided with a built-in urine analyzer. The results of analysis may be displayed or printed out in situ for personal inspection. Also, the results may be recorded in an information storage medium such as IC cards and brought to a hospital, or may be directly sent to the hospital via telecommunication network for medical diagnosis and data management.

Japanese Patent Kokai Publication No. 60-233551 discloses a toilet-type urinalysis apparatus having a sampling spoon provided within a toilet bowl. An electric urine sensor positioned at the bottom of the sampling spoon analyzes sampled urine and sends the results via a signal line to an analyzer located aside of the toilet bowl. Because of the presence of the sampling spoon, this apparatus is not suitable for use in the same manner as in the conventional toilet.

Japanese U.M. Kokai Publication No. 59-183969 describes a toilet system wherein a quantity of urine is sampled by a pump and is sent to an analyzer by way of a conduit. This system is bulky and has a problem that the conduit is apt to be clogged.

European Patent Publication No. A2-292,311 proposes a toilet-type system having a urine sampling cylinder. This system is designed such that liquid reagents are dispensed into the sampled quantity of urine. The use of liquid reagents is advantageous in that the used urine sample and the reagent may be disposed into the conventional sewage system. However, this system is unsuitable to provide a high degree of accuracy of analysis because dispensing of liquid reagent in an accurate amount is extremely difficult to perform. Moreover, handling and storage of liquid reagents is cumbersome.

In U.S. Pat. No. 4,961,431, assigned to the assignee of the present invention, there is disclosed a toilet system with health examination function. This system also uses a urine sampling pump and a conduit for sampled urine and, for reasons mentioned hereinbefore, there is a room for improvement.

Another type of toilet-type system having a built-in analyzer proposes the use of a test paper incorporating impregnated reagent.

For example, U.S. Pat. No. 4,962,550, also assigned to the assignee of the present inventions, describes various embodiments of toilet system with urine constituent measuring device. One embodiment is designed such that the user manually dips a test paper into a urine pool and then places it within an analyzer for measurement. In another embodiment, a roll of test paper is provided and the used section of the test paper roll is cut off by a cutter. In both embodiments, the used test paper or the used section of the roll is discarded into the toilet bowl and is flushed away together with toilet flushing water.

In the copending U.S. patent application Ser. No. 07/573,645, filed Aug. 27, 1990 now U.S. Pat. No. 5,111,539 and assigned to the assignee of the present invention, there is also proposed the use of a test paper. The toilet bowl is provided with a special small cavity serving to sample and store a quantity of urine. A telescoping arm carrying a test paper lowers the paper down into the urine pool in the sampling cavity and the paper soaked up with urine is then raised therefrom for measurement. The used test paper is similarly discarded into the toilet bowl for subsequent disposal into the conventional sewage system. To this end, that patent application proposes use of a test paper made from a water soluble material.

Use of water soluble test paper imposes considerable limitations on urinalysis conducted by means of a toilet-type system. Thus, in order to provide an effective information concerning the health conditions of individuals, it is desirable that the urine sample be analyzed for a plurality of biological substances. Typically, glucose, albumin, urobilinogen and occult blood are substances requiring quantitative determination. If all these substances are to be quantified in a single analysis, i.e., in one sequence of procedures, then such an test paper must be used which each is impregnated with a plurality of reagents corresponding in number to the number of substances to be detected. For example, four different kinds of reagents must be juxtaposed on a single piece of test paper. In that case, since water soluble material forming the test paper is apt to allow migration of chemicals, reagents are often mixed and contaminated with each other so that color reaction capability of respective reagents is degraded.

Commercially available on the market are those urinary testing sheets which are made from water impermeable substrate such as plastic sheet. Each sheet is provided with a plurality of reactive segments affixed thereon and spaced from each other. Each segment is made from absorbent material such as blotting paper and is impregnated with a reagent. Since respective segments on the plastic substrate are chemically isolated from each other due to the presence of intervening plastic material, there is little likelihood of reagent contamination. Use of such plastic testing sheets in combination with the toilet system having urinalysis function, however, is prohibitive since these sheets are not designed for disposal into the toilet bowl. Therefore, it is necessary for the individual user of the system to bring the used sheets to an appropriate disposal station. This procedure is cumbersome as well as unhygienic.

SUMMARY OF THE INVENTION

It is therefore an object of the present invention to provide an improved system for the assay of human-originated excrement.

Another object of the present invention is to provide a toilet system having urinalysis function which permits use of any type of testing sheets including those made from water insoluble materials.

A still another object of the invention is to provide a toilet system with urinalysis function which is provided with a sheet handling mechanism particularly suitable for the handling of those testing sheets which require special disposal after use.

A further object of the invention is to provide a toilet system with urinalysis function which is capable of providing a high degree of reliability of urinalysis.

Reliability of urinalysis depends, in the first place, upon how properly color reaction of reagent is undergone and, in the second place, upon how accurately detection of color reaction is conducted. More specifically, color reaction of reagent is a function of the amount of urine with which a predetermined amount of reagent is contacted and the timing at which measurement and detection of the thus colored reagent is performed after it has been contacted with urine.

It is, therefore, another object of the invention to provide a toilet system with urinalysis function which is capable of permitting the reagent to react with a proper amount of urine.

Still another object of the invention is to provide a toilet system with urinalysis function which is capable of performing measurement and detection of reagent at an accurate timing.

Reliability of urinalysis also depends upon the accuracy of measurement and detection of a change in color of reagent.

It is, therefore, another object of the invention to provide a toilet system with urinalysis function which is capable of effecting measurement and detection of color change of reagent with a high degree of accuracy.

In order to conduct a urinalysis with reliabilities, it is desirable to ensure that 100% pure urine is sampled. To this end, the designing requirements for the sampling cavity of a toilet bowl having urinalysis function is that it must be made as small as possible such that existing water in the sampling cavity is completely displaced by and replaced by a flow of fresh urine. The smaller the sampling cavity, the more difficult it is to properly introduce the testing sheets into the sampling cavity.

It is, therefore, another object of the invention to provide a toilet system with urinalysis function having a sheet handling mechanism which is capable of dipping a testing sheet into a urine sampling cavity with a high degree of positioning accuracy.

It has been customary to use photosensors for the purposes of detecting the degree of color reaction of testing sheets. Since photosensors are responsive to undesirable disturbing light external to the analysis, it is desirable that detection be carried out in a dark room environment.

It is, therefore, another object of the present invention to provide a toilet system with urinalysis function which is provided with an effective and simple arrangement for the provision of dark room environment.

Another object of the present invention is to provide a testing sheet handling structure particularly suitable for use as a sub-assembly for the toilet system having features described above.

According to the invention, there is provided a toilet system with urine assay function. The system comprises a toilet stool having a toilet bowl and a small urine-sampling cavity. A frame is mounted on the toilet stool to support a testing sheet handling and transfer mechanism which comprises a swingable carriage and a slidable arm supported by the carriage for linear telescoping movement. The carriage is swingable about a vertical axis between a first position in which the carriage is oriented toward the sampling cavity and a second position in which the carriage is oriented to a lateral side of the stool wherein a disposal station is provided.

In operation, a testing sheet incorporating reagents is affixed to the arm and is lowered toward the sampling cavity to thereby dip the sheet into a pool of urine provided in the sampling cavity. Thereafter, the arm is raised until the sheet is brought to the analyzer station of the system. After measurement, the carriage is rotated about its vertical axis and the used testing sheet carried thereby is discarded for disposal outside the toilet bowl.

Accordingly, the toilet system according to the invention enables the use of testing sheets which are made from water insoluble materials and which is not suitable for disposal into the toilet bowl.

The provision of swingable carriage and slidable arm provides a high degree of reliability of analysis because the testing sheet is transferred and handled with a high positioning accuracy.

The testing sheet is automatically handled and transferred throughout the dipping and measuring steps up to the final stage of disposal without resort to any manipulation by the user. Therefore, the system is easy to use and is hygienic.

Preferably, the analyzer station comprises a stationary head fixed to the frame and a movable table adapted to support the testing sheet.

This arrangement further assists in providing a high degree of reliability of urinalysis.

Preferably, the toilet system according to the invention may be provided with a mechanism for assuring precise alignment of the slidable arm with respect to the urine sampling cavity.

These features and advantages of the invention, as well as many other features and advantages thereof, will become apparent from the following description made in conjunction with the preferred embodiments thereof with reference to the accompanying drawings.

BRIEF DESCRIPTION OF THE DRAWINGS

FIGS. 11 and 12 illustrate alternative forms of sheet clamp;

FIGS. 15 and 16 are cross-sectional views showing the detail of the stationary head and the movable table;

FIG. 17 is a rear view of the stationary head taken along the line XVII—XVII of FIG. 15;

FIGS. 18A–18K are schematic representation of sequence of events performed by the toilet system of the invention;

Throughout different drawings, like parts and components of the system are indicated by like reference numerals.

DESCRIPTION OF THE PREFERRED EMBODIMENTS

Reference will now be made in detail to the first embodiment of the invention as illustrated in FIGS. 1–18.

Figure 1:
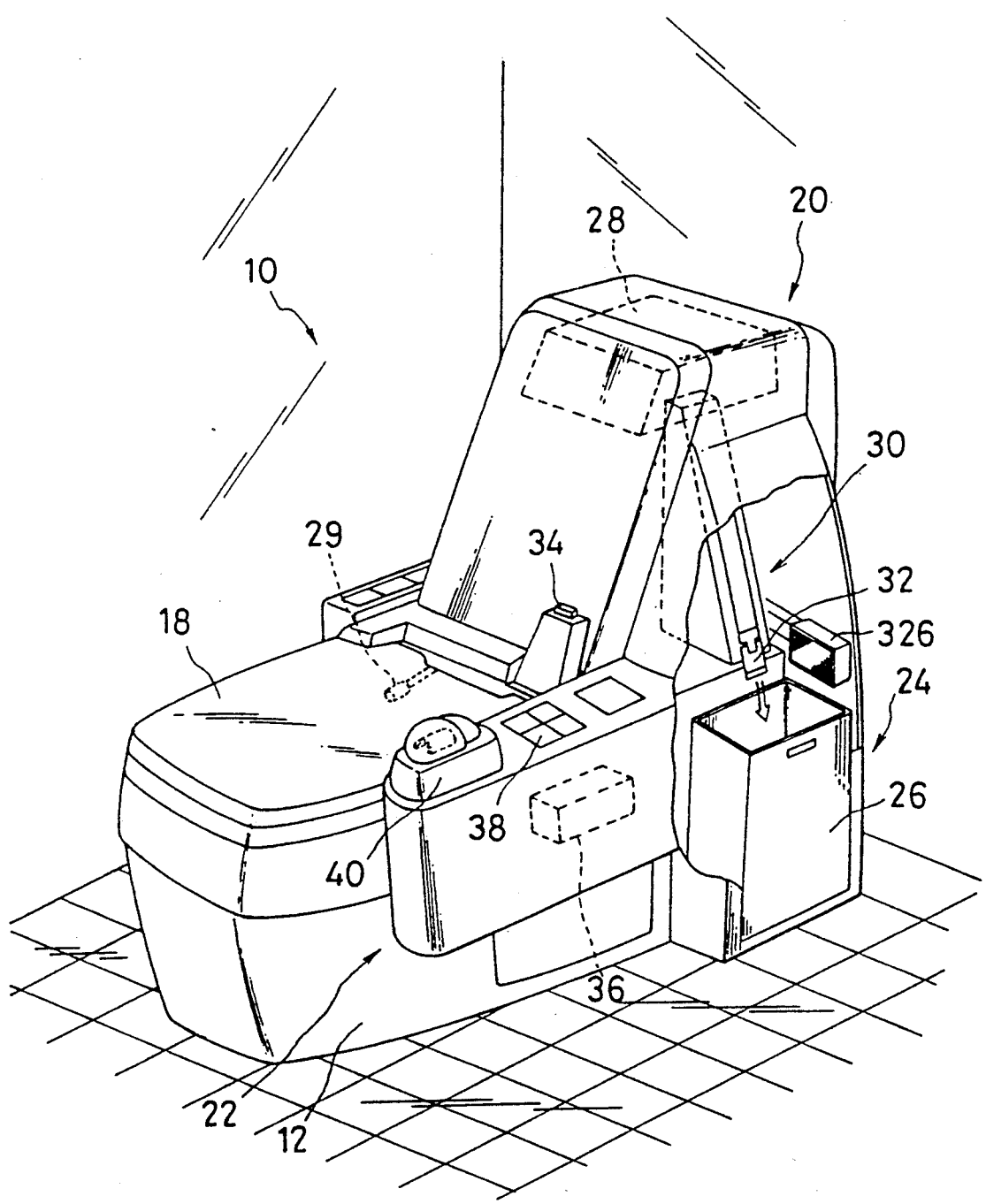
FIG. 1 is a perspective view, partly cut away, showing the overall arrangement of the toilet system according to the preferred embodiment of the invention.

Referring primarily to FIG. 1, there is shown a toilet system, generally indicated by the reference numeral 10, provided with urine sampling and assaying function. The toilet system 10 may typically be installed in a bathroom of a home. However, the system may also be installed in hospitals, clinics, facilities for the aged people, or any other appropriate public or private facilities.

Figure 3:
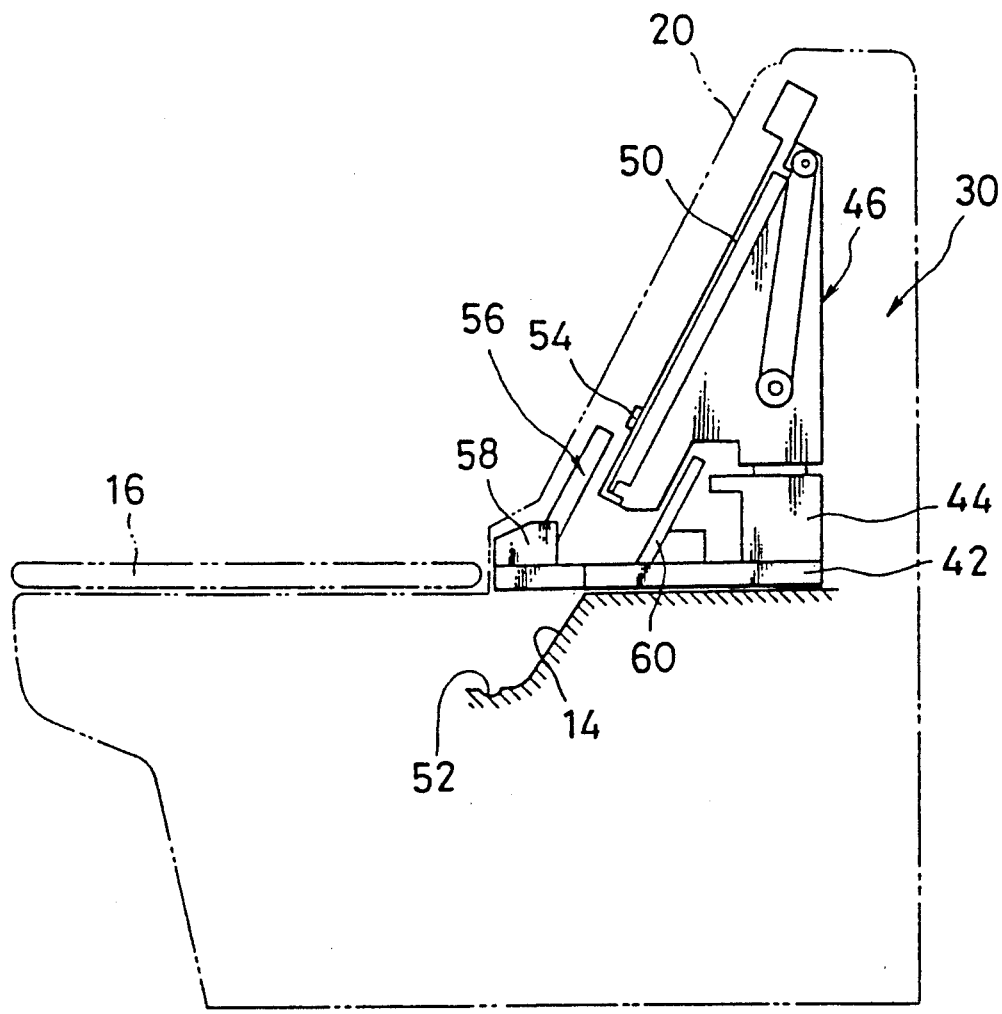
FIG. 3 is a schematic side elevation of the sheet transfer mechanism shown in FIG. 2.
Figure 4:
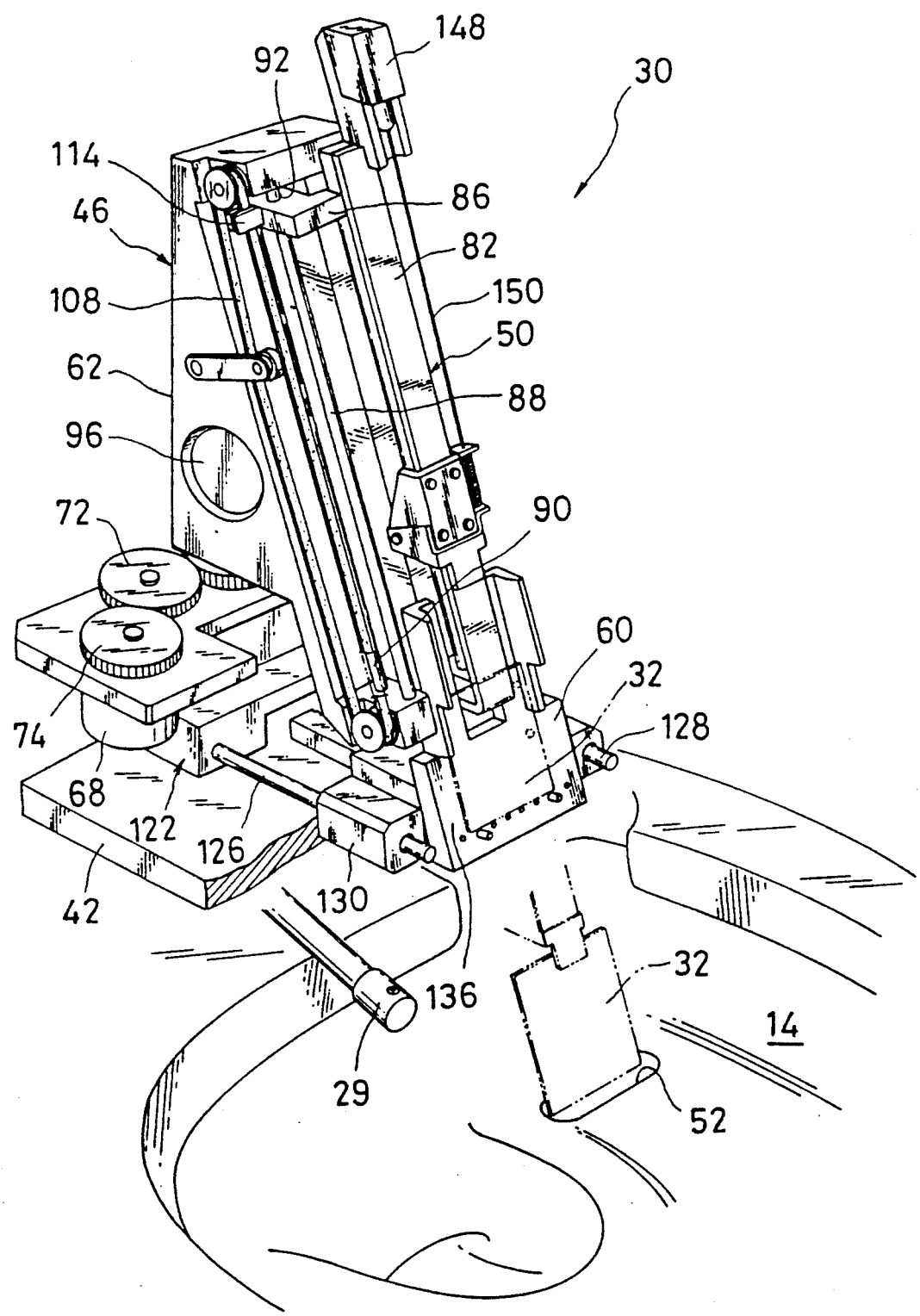
FIG. 4 is a perspective view of the sheet transfer mechanism as used in the toilet system shown in FIG. 1.

The toilet system 10 includes a base 12 serving as a toilet stool defining a toilet bowl 14 which is best shown in FIG. 4. The toilet stool 12 is provided with a conventional swingable seat 16, shown schematically in FIG. 3, and is closed at its top by a swingable cover 18 as well known in the art.

As illustrated in FIG. 1, the toilet system 10 is provided with a rear housing 20 and a lateral housing 22, connected with each other by a housing 24 for a trash box 26. A cistern 28 is positioned at the upper part of the rear housing 20 and is connected to the toilet bowl 14 for flushing thereof in the conventional manner. The rear housing 2˜ may also be used for installing therein a conventional shower system for rinsing the anus and pubes of the user, a shower nozzle of which is shown at 29 in FIG. 1.

As shown in FIG. 1, a testing sheet transfer and handling mechanism 30 featuring the present invention is mainly housed within the rear housing 20. In FIG. 1, the sheet transfer mechanism 30 is shown as being swung to its second position facing the trash 26 for disposal of a testing sheet 32, which will be described later in more detail with reference to FIG. 10. The testing sheet 32 is adapted to be inserted by the user through an inlet slot 34 provided in the frontal part of the housing 20. An electronic control box 36 for the sheet transfer mechanism 30 as well as for a urine analyzer is mounted within the lateral housing 22. The housing 22 is also provided with a display 38 of the analyzer and a conventional digital sphygmomanometer 40. Conventional IC card reader-writer and printer may be installed in the housing 22 for the processing and recording of health data obtained by analysis and measurement.

Figure 2:
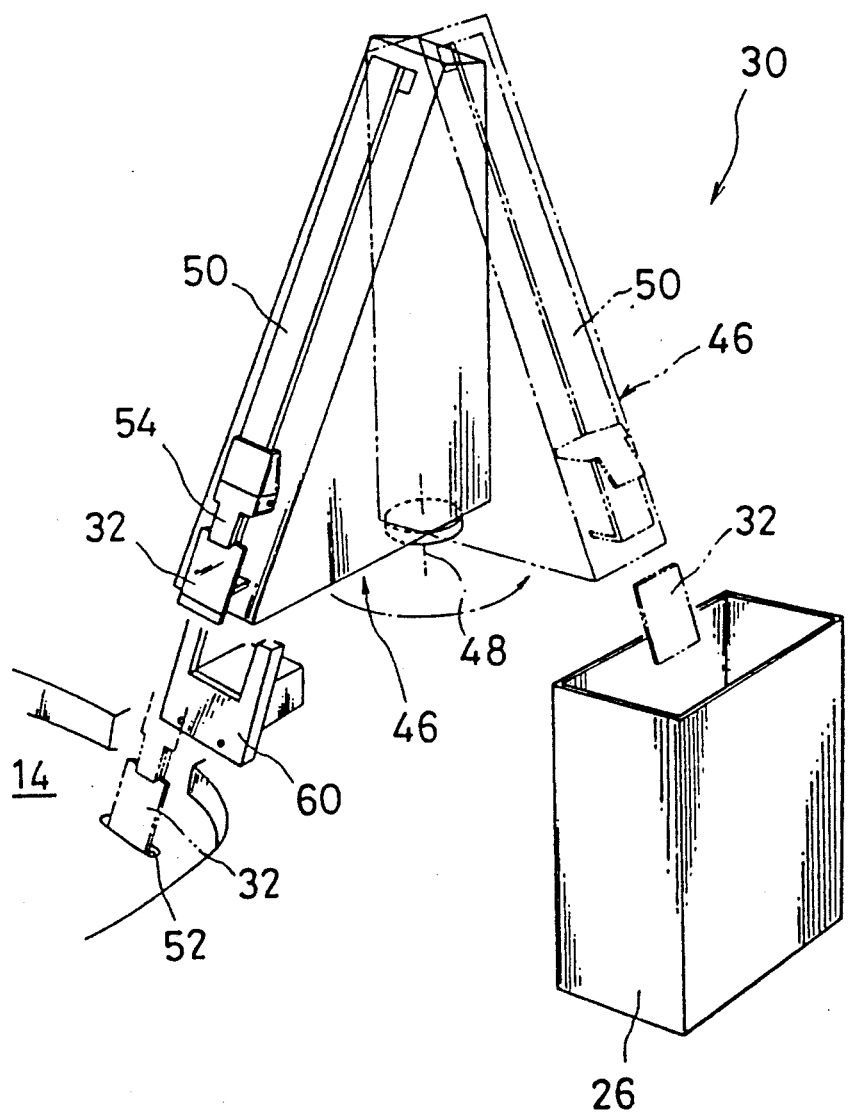
FIG. 2 is a schematic perspective view of the sheet transfer mechanism as used in the toilet system shown in FIG. 1, with the solid and ghost lines showing two extreme positions of the carriage.

The overall structure of the sheet transfer mechanism 30 and an analyzer station of the urine analyzer, as we as the principle of operation thereof, will be described first with reference to FIGS. 2 and 3.

Figure 9:
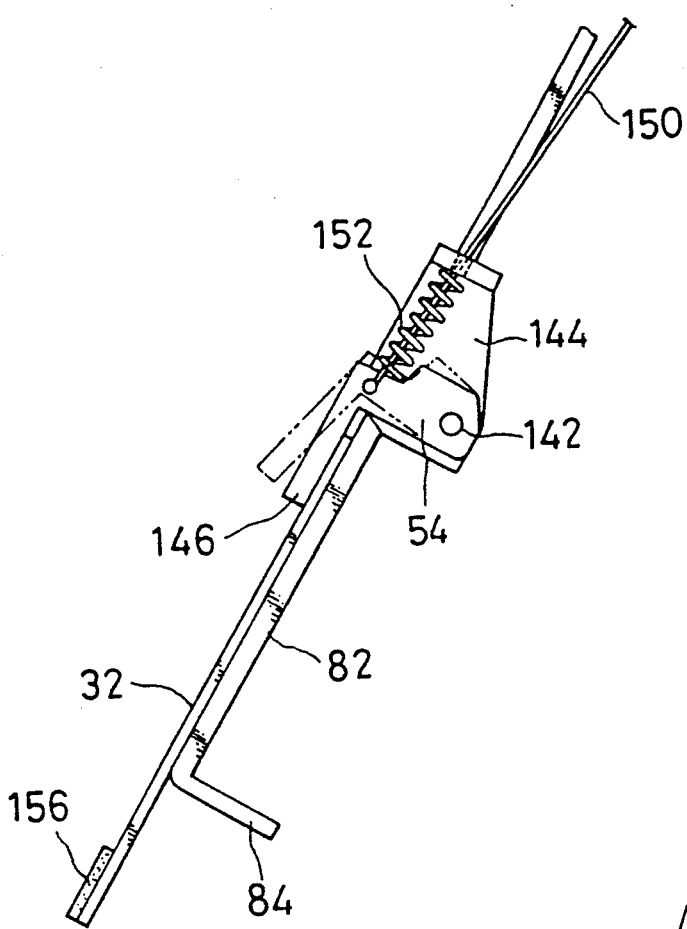
FIG. 9 is a side elevation of a sheet clamping mechanism.

As illustrated in FIG. 3, the transfer mechanism 30 includes a frame 42 fixed on the toilet stool 12. In the illustrated embodiment, a separate support 44 is mounted to the frame 42. It should be understood, however, that the support 44 may be formed as an integral part of the frame 42, thereby forming part thereof. As schematically shown in FIG. 2, the mechanism 30 is comprised of a swingable carriage 46 mounted to the support 44 for pivoting movement about a vertical axis 48 and of a slidable arm 50 supported by the carriage 46 for translational movement along a plane passing through the axis 48. Preferably, the axis of the arm 50 is slightly inclined with respect to the vertical pivot axis 48. The carriage 46 is swingable between a first position shown by the solid line in FIG. 2 and a second position indicated by the ghost line. In the first position, the carriage 46 is oriented toward a small narrow elongated cavity 52 which is formed on the surface of the toilet bowl 14 and which serves as a urine sampling cavity. In the second position, the carriage 46 is directed to the trash box 26. A sheet clamping member 54, described later in more detail with reference to FIG. 9, is mounted to the slidable arm 50 at a level slightly above the lowermost end thereof.

The analyzer station, generally designated in FIG. 3 by the reference numeral 56, of the urine analyzer comprises a stationary head 58 fixed to the frame 42 and a movable table 60 supported by the frame 42 for sliding movement to and away from the stationary head 58. The movable table 60 is arranged to slide parallel to the center line of the toilet system.

It will be understood that, with this arrangement, lowering of the arm 50 with a testing sheet 32 clamped by the clamping member 54 and with the carriage 46 situated in its first position will cause the lower part of the testing sheet 32 to be brought into contact with a pool of urine formed in the sampling cavity 52. The testing sheet thus soaked up with urine is then lifted by raising the arm 50 until the testing sheet 32 is situated at the level of the analyzer station 56. The movable table 60 is then moved forward and measurement of the testing sheet is effected. After analysis, the carriage 46 is turned as shown in FIG. 2 and the used testing sheet is discarded into the trash box 26. The above mentioned sequence of events will be described later in more detail with reference to FIG. 18.

Referring primarily to FIGS. 4-9, the foregoing structure will now be described in a greater detail.

Figure 5:
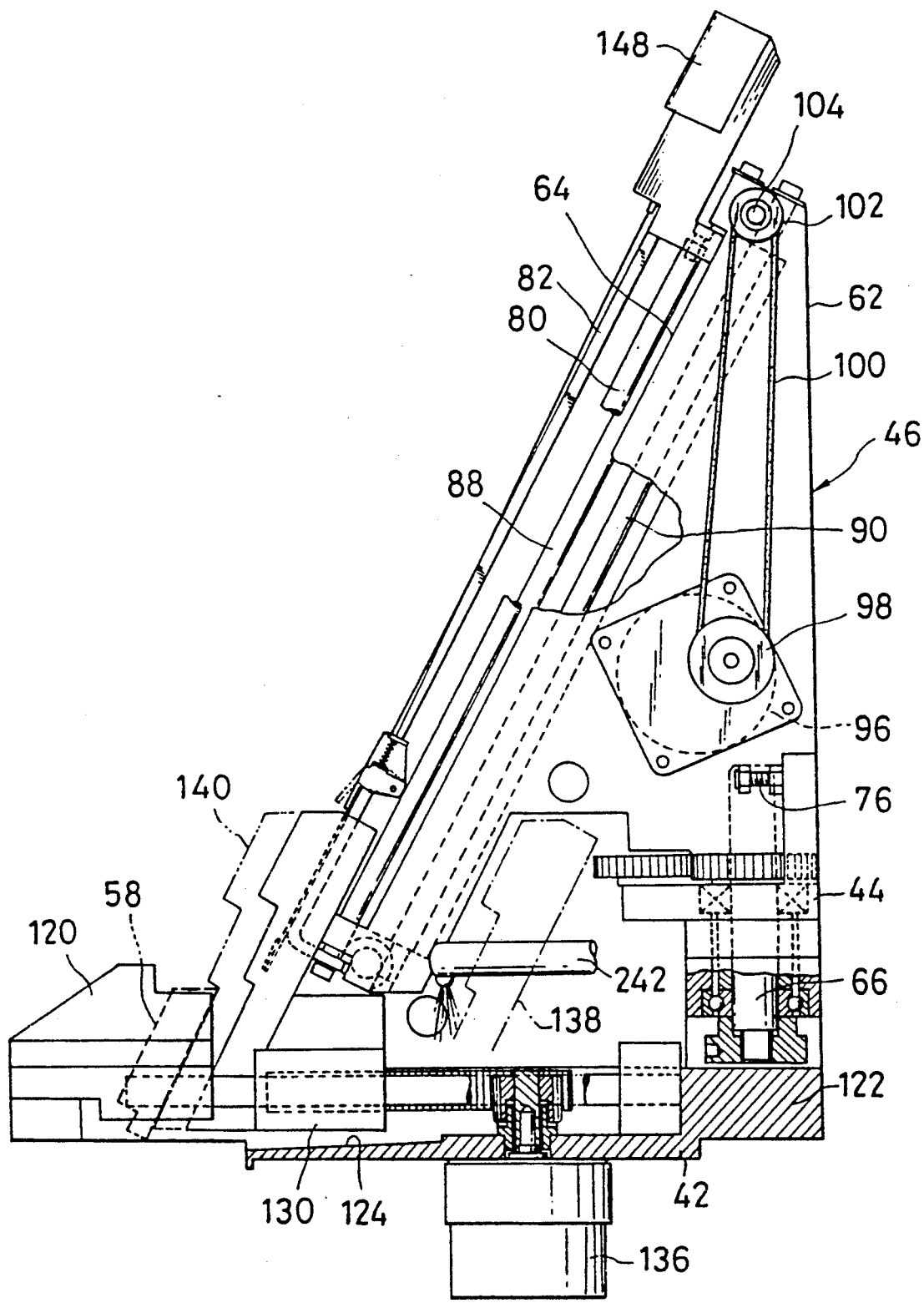
FIG. 5 is a side elevation, partly cut away, of the sheet transfer mechanism, with the dotted and ghost lines showing two extreme positions of the movable table.
Figure 6:
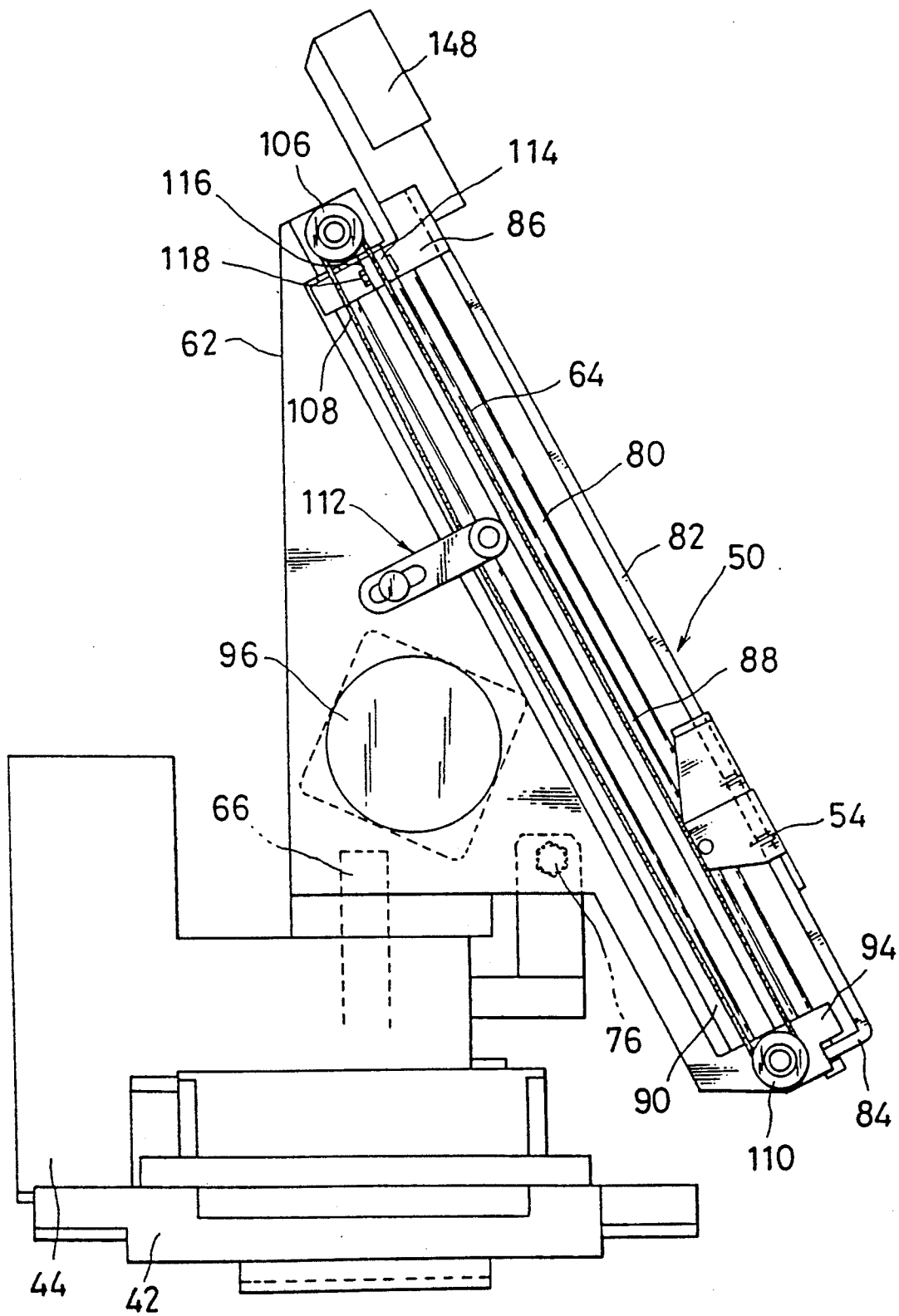
FIG. 6 is a front elevation of the sheet transfer mechanism, carriage rotated to its second position.
Figure 7:
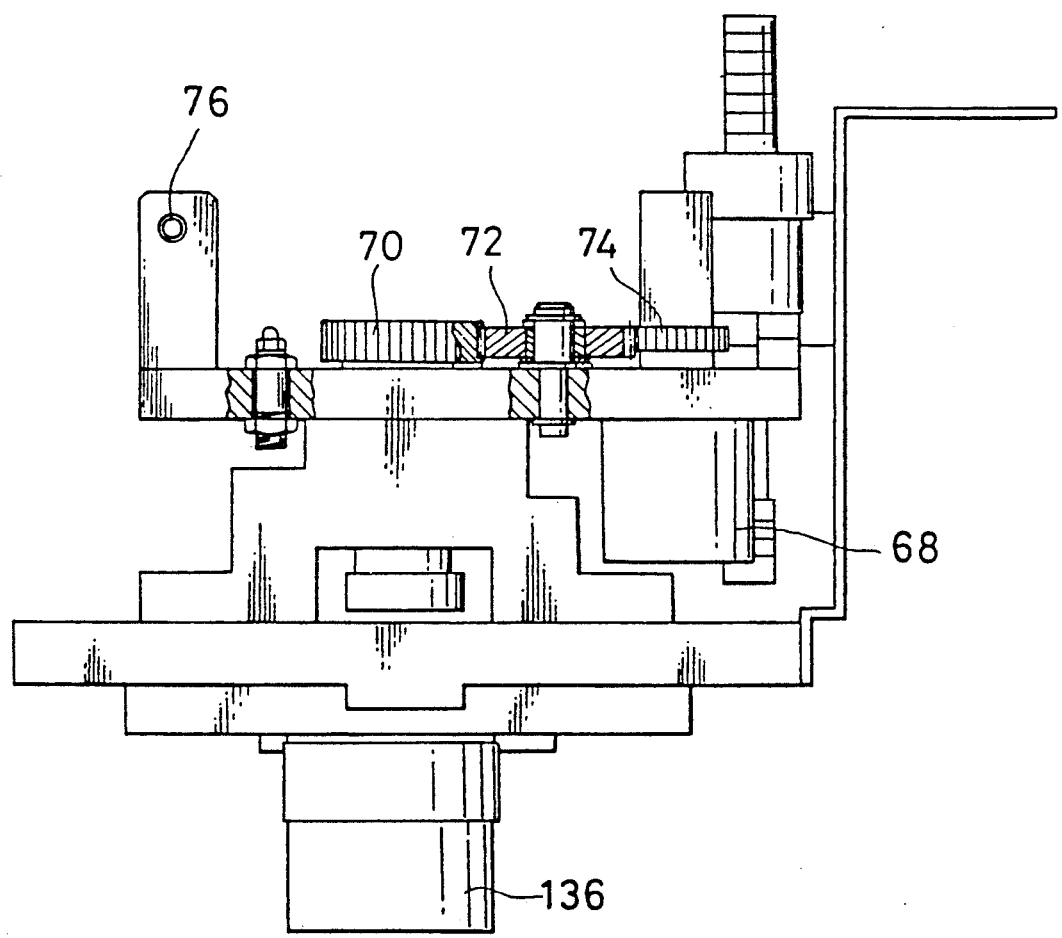
FIG. 7 is a rear elevation, partly cut away, of the sheet transfer mechanism, with carriage and arm removed for clarity.

The carriage 46 is somewhat triangular in side elevation and is defined by a vertical rear wall 62 and an inclined frontal wall 64 (FIGS. 5 and 6). The carriage 46 has a pivot 66 journaled to the support 44 as best shown in FIG. 5. The carriage 46 is adapted to be rotated about the pivot 66 having its axis 48 for about 90 degrees by means of an AC motor 68 mounted to the support 44. To this end, a gear 70 keyed to the pivot 66 is in mesh with an intermediate gear 72 which, in turn, is in meshing engagement with an output gear 74 of the motor 68. Therefore, rotation of the motor 68 in one direction will cause the carriage 46 to rotate in the same direction about its axis 48 and rotation of the motor in the reverse direction will cause the carriage to swing in the reverse direction. The swinging movement of the carriage 46 in the counterclockwise direction as viewed in the top plan view is limited by an adjustable abutment 76 best shown in FIG. 5 and the movement thereof in the clockwise direction is limited by a similar abutment (not shown in FIG. 5 but indicated at 78 in FIG. 29). The control circuit of the motor 68 is designed to sense the engagement of the carriage 46 with either of the abutments 76 and 78 by way of a torque limiter circuit thereof and to stop the motor after a lapse of predetermined period of time. Therefore, the carriage 46 is correctly oriented at its first and second positions mentioned hereinbefore with reference to FIG. 2.

In the illustrated embodiment, the slidable arm 50 is made in the form of a bow of a violin as will be best understood from FIG. 6 and includes a rod 80 and an elongated metal plate 82 having a lower end 84 bent at a right angle and joined to the rod 80. The upper ends of the rod 80 and the metal plate 82 are joined or fastened to a slide block 86 so that the members 80, 82 and 86 together make up the unitary arm 50. The guidance of the slidable arm 50 for its telescoping sliding movement with respect to the carriage 46 is twofold. First, the slide block 86 of the slidable arm 50 is guided by a pair of parallel guide rods 88 and 90 firmly supported at their ends by the carriage as best shown in FIG. 4. To this end, the slide block 86 is provided with a pair of through bores (one of which is shown in FIG. 4 at 92) slidably accommodating the guide rods 88 and 90. In the second place, the rod 80 of the arm 50 slidably extends through a bore (not shown) formed across the lower extension 94 of the carriage 46 as best shown in FIG. 6. The telescoping sliding movement of the arm 50 is carried out by a stepping motor 96, with a reduction gear mechanism, which is mounted within a lateral recess of the carriage 46 and which moves the arm 50 up and down via a belt and pulley assembly. To this end, the motor 96 has a clogged output pulley 98 over which a clogged belt 100 is entrained at one side of the carriage 46. Rotation of the motor 96 is transmitted to a pulley 102 keyed to an end of a shaft 104. Keyed to the opposite end of the shaft 104 situated at the other side of the carriage 46 is a further pulley 106 as best shown in FIG. 6. A clogged belt 108 is entrained between the pulley 106 and a further pulley 110 rotatably supported by the lower extension 94 of the carriage 46. Preferably, a tension roller assembly 112 is provided to take up any slack in the belt 108. As shown in FIGS. 4 and 6, one of the runs of the belt 108 is securely clamped to the slide block 86 by using, for example, a clamping plate 114 cooperating with a correspondingly shaped lateral projection 116 of the block 86 and fastened thereto by screws 118. With this arrangement, the slidable arm 50 is lowered and raised as the motor 96 is rotated in one or other direction. In FIGS. 5 and 6, there is shown the arm 50 as lifted to the uppermost position thereof, while FIG. 4 shows by the ghost line the arm 50 as being lowered to dip the testing sheet 32 partly into the urine pool.

Figure 8:
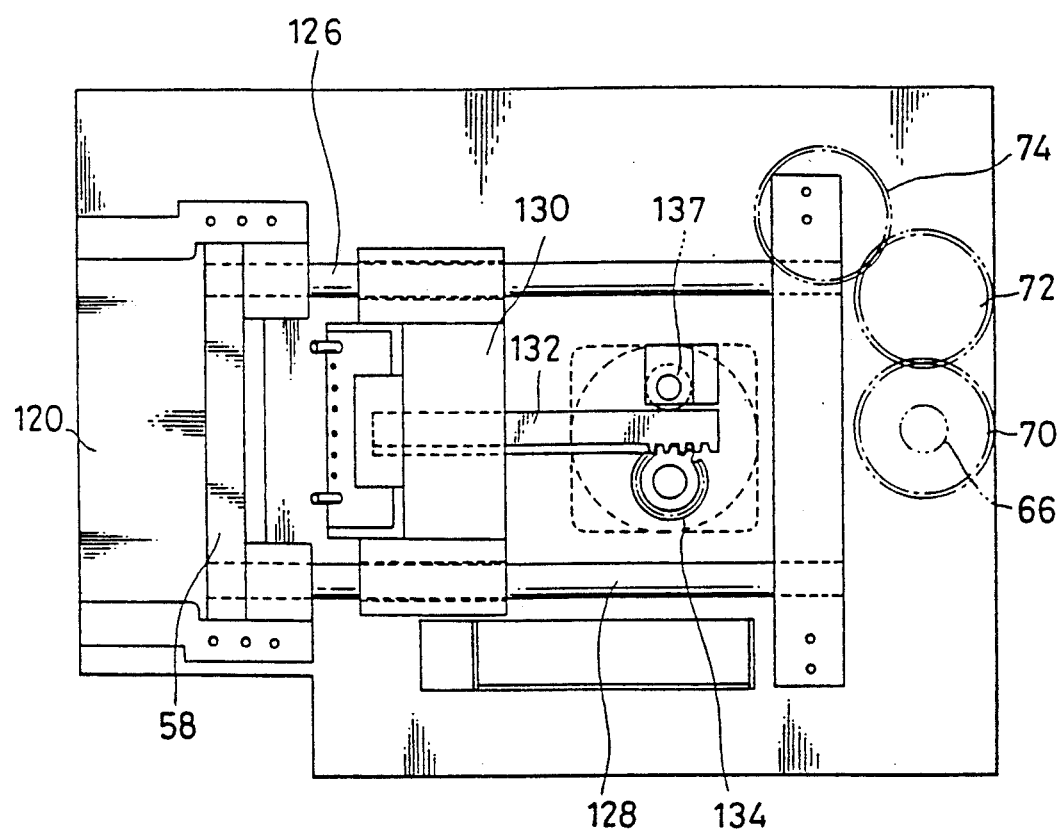
FIG. 8 is a top plan view of the analyzer station, with the carriage removed for clarity.

The analyzer station 56 shown schematically in FIG. 3 will now be described in detail with reference to FIGS. 4, 5 and 8. As best shown in FIG. 5, the frame 42 may include a frontal block 120 and a rear block 122 forming an integral part thereof and spaced apart from each other by an intermediate recess 124. A pair of parallel guide rods 126 and 128 (FIG. 4) extend across the recess and are firmly supported by the frame 42 between the spaced blocks 120 and 122. The stationary head 58 of the analyzer station 56, which will be described later with reference to FIGS. 15–17, is secured to the frontal block 120 as shown in FIGS. 5 and 8. As best shown in FIG. 4, the guide rods 126 and 128 extend through a slide block 130 to slidably support and guide the slide block 130, thereby enabling the block 130 to slide in the back and forth directions. The slide block 130 is driven by a rack and pinion arrangement (FIG. 8) having a rack 132 fixed at an end thereof to the slide block 130 and a pinion 134 which is driven by a stepping motor 136 (FIG. 5). Preferably, the rack 132 is backed up by a counter roller 137.

The movable table 60 forming part of the analyzer station 56 is secured to the slide block 130 as best shown in FIGS. 4 and 5. The table 60 has an inclined frontal surface 136 adapted to support and locate the testing sheet 32. Further detail of the movable table 60 will be set out later with reference to FIGS. 13 and 14. It will be readily understood that, by rotating the motor 136 in one or other direction, the movable table 60 is moved to or away from the stationary head 58. In FIG. 5, the solid line indicates the table 60 as being in its position in which the table surface 136 is brought into registration with the frontal surface of the arm 50, the dotted line 138 indicating the table 60 in its retracted position, the ghost line 140 indicating the table 60 as it is brought into contact with the stationary head 58.

As shown in FIGS. 4, 5 and 9, the clamping member 54 is pivoted at 142 to a bent sheet metal member 144 which is fastened to the plate 82 of the slidable arm 50. The clamping member 54 has a swingable finger 146 designed to cooperate with the plate 82 to clamp the upper end of the testing sheet 32 against the plate 82 as shown in FIG. 9. The clamping member 54 is opened by a solenoid actuator 148 mounted to the upper end of the arm 50 and acting through a cable 150. A return spring 152 is provided to bias the clamp 54 in its normally closed position. With this arrangement, the testing sheet 32 is positively held in place on the arm 50 so that any misalignment of the sheet which would otherwise occur with respect to the arm 50 due to the gravity or mechanical shock acting on the sheet can be avoided. Therefore, it is possible to position the testing sheet 32 within the urine pool with a high degree of accuracy.

Figure 10:
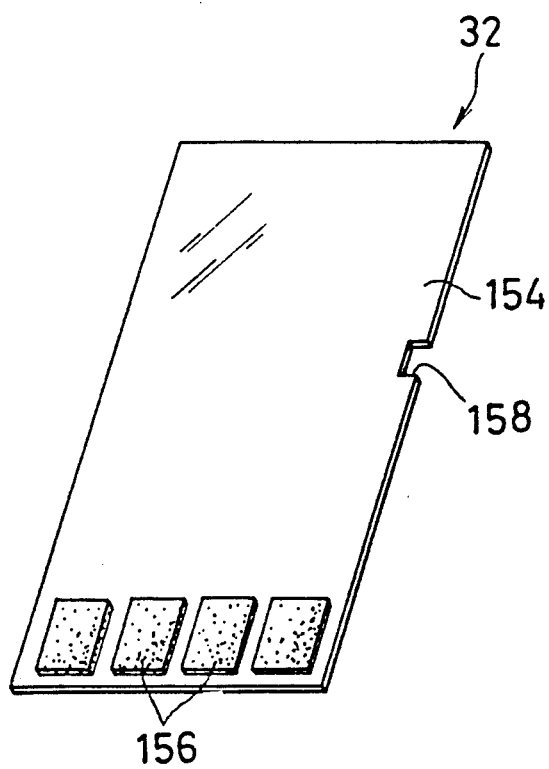
FIG. 10 is a perspective view in an enlarged scale of a testing sheet.

In FIG. 10, there is shown a typical testing sheet suitable for use in urinalysis performed by the toilet system according to the invention. The sheet 32 includes a substrate 154 made, for example, from plastics such as polyvinylchloride. Affixed to the substrate are a plurality of patches 156 spaced apart from each other. Each patch 156 may be made from absorbent material, such as blotting paper, which is impregnated with a reagent. In the testing sheet 32 shown, there are four such patches so that glucose, albumin, urobilinogen and occult blood can be detected and determined at one time by a single testing sheet. When the reagent contained in the patches 156 is contacted with urine, it undergoes color reaction thereby resulting a change in color of the patches. Degree of color change is proportional to the content of biological substances contained in urine and, therefore, is subjected to detection for quantification of substances. For reasons described later, each sheet 32 is preferably provided with a cutout 158 at one side thereof. The cutout 158 is slightly offset upwardly with respect to the transverse center line of the sheet 32.

FIGS. 11 and 12 illustrate alternative forms of clamping mechanism. Referring to FIG. 11, the mechanism includes a fixed jaw 160 and a movable jaw 162 moved by the cable 150. A pair of friction pads 164 are attached to the jaws 160 and 162 to securely hold the testing sheet. Alternatively, a further presser member 166 may be pivoted at 168 to a bell crank 170 as shown in FIG. 12. This arrangement ensures that the clamping mechanism accommodates any changes in thickness of the testing sheet thereby to provide a face contact.

Figure 13:
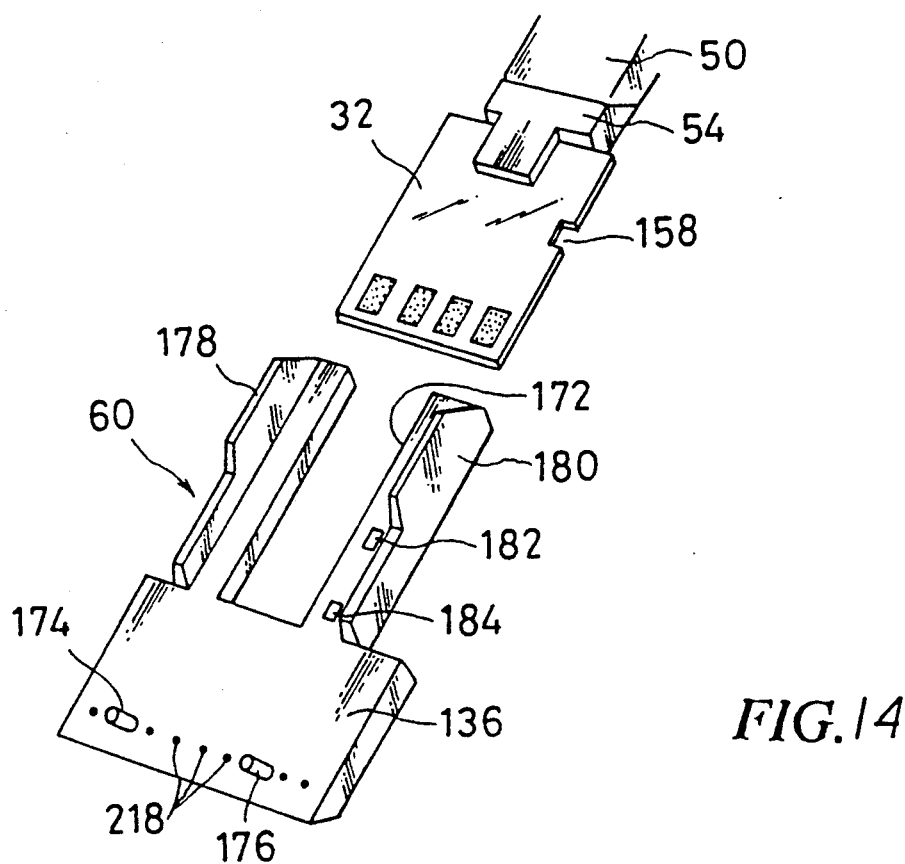
FIG. 13 is a perspective view of the movable table.

Referring to FIG. 13, the movable table 60 is provided with a central recess 172. This is to enable the table 60 to slide back and forth without interference with the lower parts of the carriage 46 and arm 50 as best shown in FIG. 4. The table 60 is further provided at its lower end with a pair of upright stopper pins 174 and 176 to facilitate longitudinal positioning of the testing sheet 32. Accordingly, the testing sheet 32 placed on the inclined table surface 136 will slide down therealong by gravity until it engages the pins 174 and 176 whereupon the sheet is accurately positioned with respect to the opposing stationary head 58. The table 60 is also provided with a pair of lateral guides 178 and 180 for lateral positioning of the sheet 32. These guides 178 and 180 are defined by forwardly diverging tapered inner surfaces as shown so as to ensure that the testing sheet thrown into the inlet slot 34 (FIG. 1) is readily centered with respect to the table 60. A pair of spaced photosensor 182 and 184 are mounted at a side of the table 60 to detect whether the sheet 32 is correctly placed on the table 60. The electronic control 36 associated with these sensors determines the correct placement when, for example, the upper sensor 182 detects the cutout 15B in the sheet 32. If the lower sensor 184 detects the output 15B, the control 36 determines that the sheet is placed upside down. If none of the sensors detects the cutout 158, then it will be judged that the sheet is placed in reverse. Any misplacement of the testing sheet will be indicated by any suitable means to the user.

Figure 14:
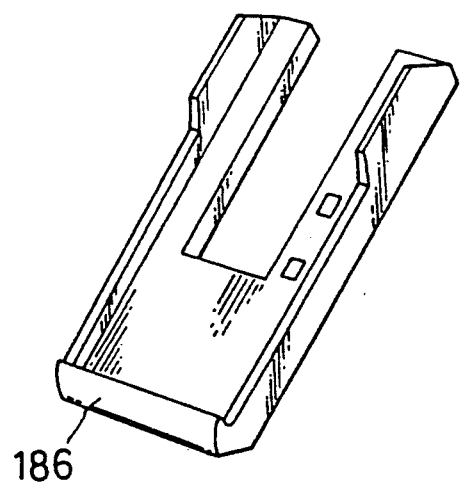
FIG. 14 is a perspective view showing alternative form of the movable table.

FIG. 14 shows an alternative form of the table 60 wherein the lower stop for the sheet is made in the form of a rib 186.

Referring now to FIGS. 15–17, the detail of the stationary head 58 will be described. As shown in FIG. 17, the head 58 is provided with four pairs of openings 188 and 190, with each pair corresponding to one reagent patch 156 of the testing sheet 32. In each pair of openings, a light emitting diode (LED) 192 and a photosensor 194 are received respectively as shown in FIG. 15. The rear surface of the head 58 has a light shielding flange 196 encircling the array of openings 188 and 190 and facing the movable table 60. As the movable table 60 is advanced toward the head 58 and is brought in contact therewith as shown in FIG. 16, the upper part of the testing sheet 32 is sandwiched between the head 58 and the table 60 thereby securely clamping the sheet 32 therebetween, with the reagent patches 156 held in spaced parallel relationship from the LEDs and photosensors. At the same time, a dark room environment is formed between the head 58 and the table 60 as shown, in which detection and measurement are performed. Thus, LEDs 192 emit infrared light and the reflected light is sensed by photosensors 194 which issue signals indicative of the degree of color reaction of the reagent patches 156. The signals are sent to the control 36 which determines the content of biological substances contained in urine and indicates the results to the display 38. Because in this manner the detection is conducted in a dark room environment in the absence of any disturbing light rays external to the measurement, the accuracy of measurement is considerably improved.

Sequence of events performed by preferred embodiment of the toilet system according to the invention will be described with reference to FIGS. 18A–18K in combination with FIGS. 19–25.

Figure 18A:
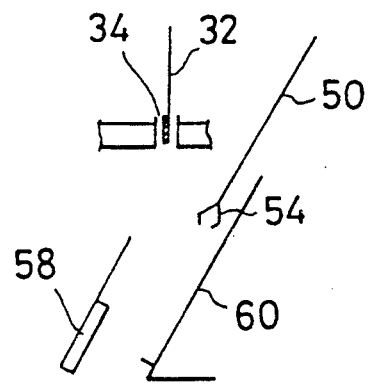

Referring to FIG. 18A, when, in response to a signal from a seat sensor associated with the toilet seat, the control 36 senses the fact that the user is seated on the toilet stool, it operates to bring the sheet transfer mechanism 30 and the analyzer station 56 into respective initial position as shown. In this position, the swingable carriage 46 is oriented forwardly as shown in FIG. 3, with the slidable arm 50 raised at it topmost position, with the movable table 60 moved to a location situated below the inlet slot 34. As the user slips the testing sheet 32 into the slot 34, the sheet 32 falls upon the inclined table surface 136 by being guided by the lateral guides 178 and 180 (FIG. 13). The sheet 32 slides along the table surface and abuts against the stopper pins 174 and 176 whereby the sheet is correctly positioned on the table 60 in both the lateral and vertical directions. Then, the control 36 operates in response to the signals from the photosensors 182 and 184 to determine whether the sheet 32 has been inserted in a proper orientation, as described before with reference to FIG. 13. If it is judged that the user has improperly installed the sheet, this is indicated to the user and the sheet is clamped by the clamp 54 and is rejected to the trash box 26 after swinging the carriage 46 for about 90 degrees.

Figure 18B:
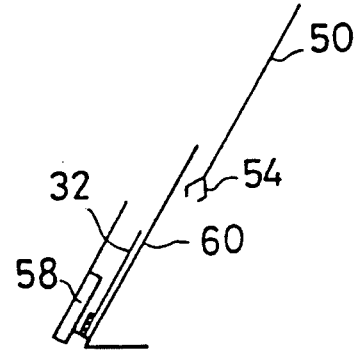

If proper placement of the sheet 32 is detected, preliminary measurement of the sheet is conducted as shown in FIG. 18B, with the movable table 60 brought into contact with the stationary head 58. This preliminary measurement is primarily intended to determine whether or not the sheet is not degraded. Another purpose of preliminary measurement is to detect and memorize the initial color of the reagent patches prior to the occurrence of color reaction.

Figure 18C:
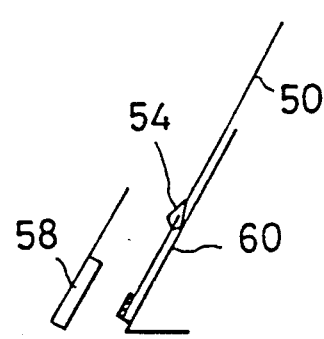

After the preliminary measurement, the table 60 is retracted as illustrated in FIG. 18C until the sheet 32 supported by the table is brought into registration with the clamp 54. The system then proceeds to clamp the sheet 32.

Figure 18D:
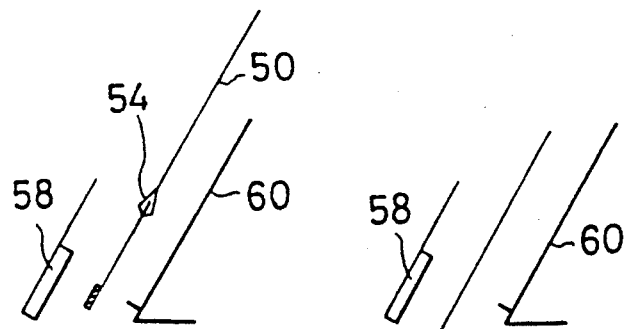

When the sheet is clamped, the table 60 is retracted further as shown in FIG. 18D and the entire system stands by in this position until receipt of instructions of the user. This position may be termed as the stand-by position. The provision for this stand-by position is advantageous in that the response of the system to subsequent events is considerably improved.

Figure 18E:
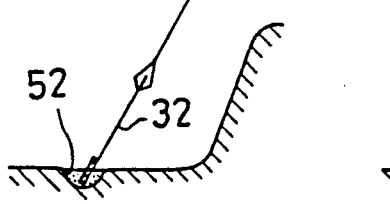

As the user presses on a start button after urination, the slidable arm 50 is lowered with the testing sheet 32 held by the clamp 54 until the reagent patches 156 are dipped into the urine pool in the sampling cavity 52 as illustrated in FIG. 18E to soak up the patches with urine.

Figure 18F:
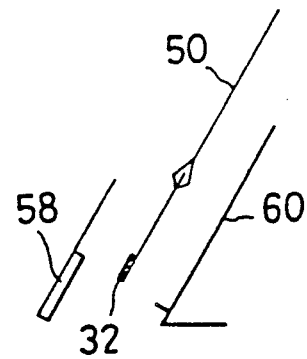

Then, the soaked sheet is raised by retracting the arm 50 upwards as shown n FIG. 18F.

Figure 19A:
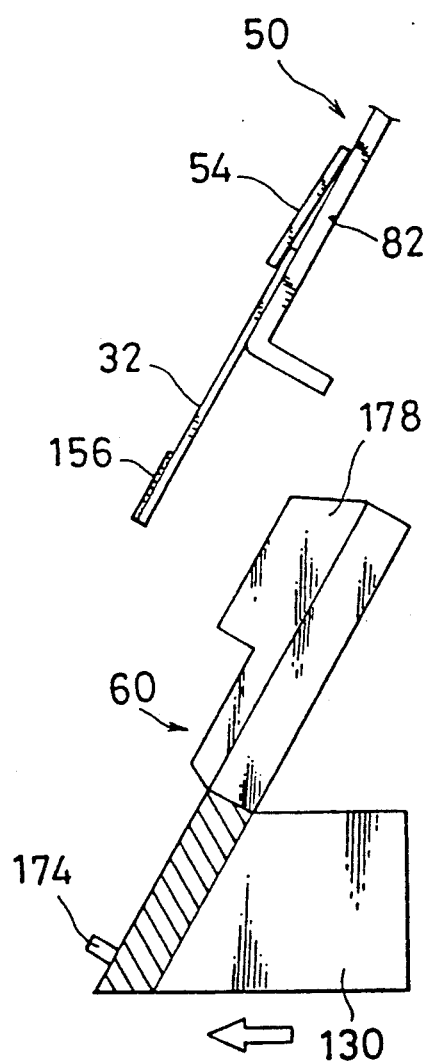
FIGS. 19A and 19B are side elevation, party cut away, showing the manner in which the testing sheet is placed on the movable table.
Figure 19B:
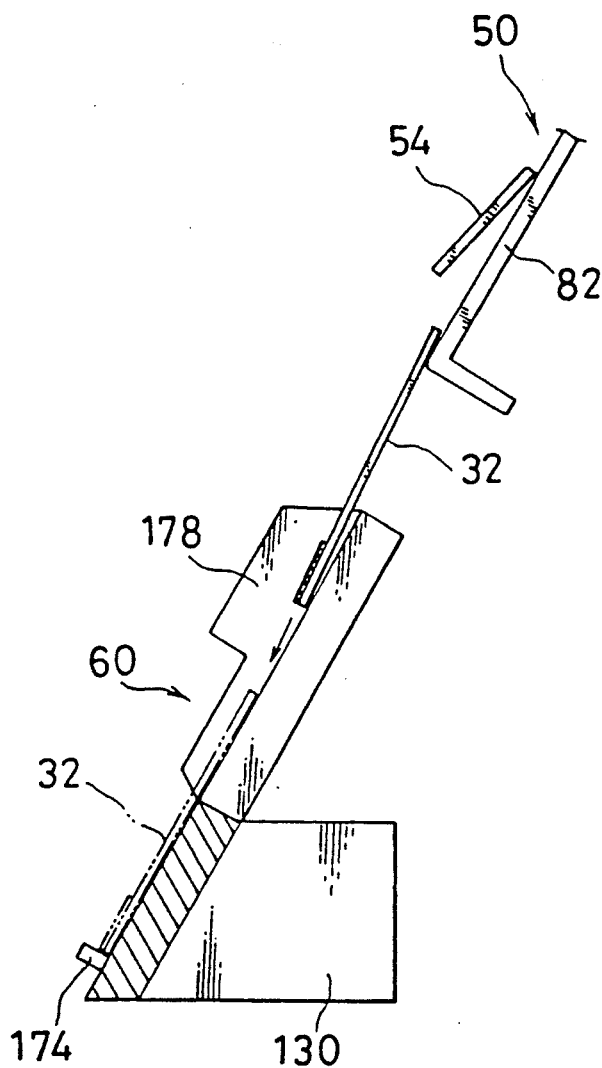

The table 60 is then moved forward until the sheet is situated above the table surface as illustrated in FIG. 18G. More specifically, after the arm 50 with its sheet 32 held thereon is raised as shown in FIG. 19A, the table 60 is moved forwardly enough to bring the stopper pins 174 and 176 ahead of the lower end of the overlying testing sheet 32 as shown in FIG. 19B. This arrangement is preferable because the distance of fall through which the sheet must to travel before reaching the table surface is minimized. This contributes to avoid the danger of the sheet to lose its controlled position during fall and to thereby improve the positioning accuracy. The solenoid actuator 148 is then actuated to release the sheet from the clamp 54 whereby the sheet is allowed to fall upon the table surface 136. The sheet then slides along the table surface to abut against the stoppers so that the sheet is automatically located at its proper position as indicated by the ghost line in FIG. 19B.

Thereafter, the arm 50 is raised and the table 60 moved until it is brought into contact with the stationary head 58 as indicated in FIG. 18H. In this position, a complete dark room environment is provided as mentioned before and the sheet is subjected to measurement in such an environment.

After analysis, the table is moved backward as illustrated in FIG. 18I and the arm 50 is then lowered to allow the clamp 54 to again grip the sheet.

Then, the table 60 is fully retracted as shown in FIG. 18J.

Finally, the carriage 46 is rotated for about 90 degrees with the sheet 32 being held by the clamp as illustrated in FIG. 18K. The clamp is then released to discard the used testing sheet into the trash box for subsequent disposal.

In this manner, the toilet system with urinalysis function according to the invention enables the use of testing sheets which are made from water insoluble materials and which, for this reason, are not suitable for disposal into the toilet bowl.

The testing sheets are automatically handled and transferred throughout the dipping and measuring steps up to the final stage of disposal without resort to any manipulation by the user. Therefore, the system is easy to use even for the aged or handicapped people and is hygienic.

Further, a high degree of sheet positioning accuracy is achieved by the use of the swingable carriage and the slidable arm in combination with the movable table structure. This is important because the accuracy of positioning of testing sheet affects the results of urinalysis.

Figure 20A:
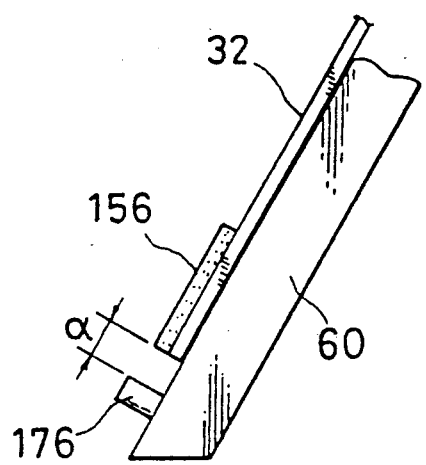
FIGS. 20A and 20B are side views showing the preferable sequence in which the table is disengaged from the testing sheet.
Figure 20B:
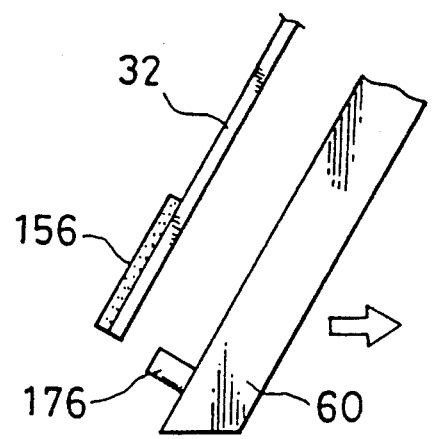
Figure 21:
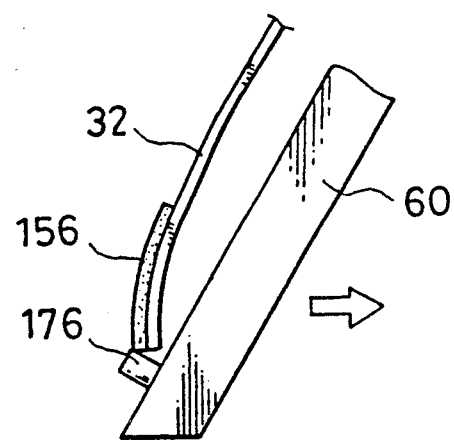
FIG. 21 is a side elevation showing an undesirable situation in which the testing sheet is dragged by the moving table.

Referring again to FIGS. 18I and 18J, if the table 60 to is be moved backward immediately after clamping of the sheet, the stopper pins 174 and 176 of the moving table as engaged with the lower end of the sheet will cause the sheet to warp and will finally cause the sheet to snap as movement of the table proceeds. This is shown in FIG. ˜1. Such snap action of the sheet is undesirable because the system components are spoiled by urine droplets. To avoid this, it is preferable to first raise the arm 50 through a small distance alpha as shown in FIG. 20A and then commence the backward movement of the table as shown in FIG. 20B.

Figure 22:
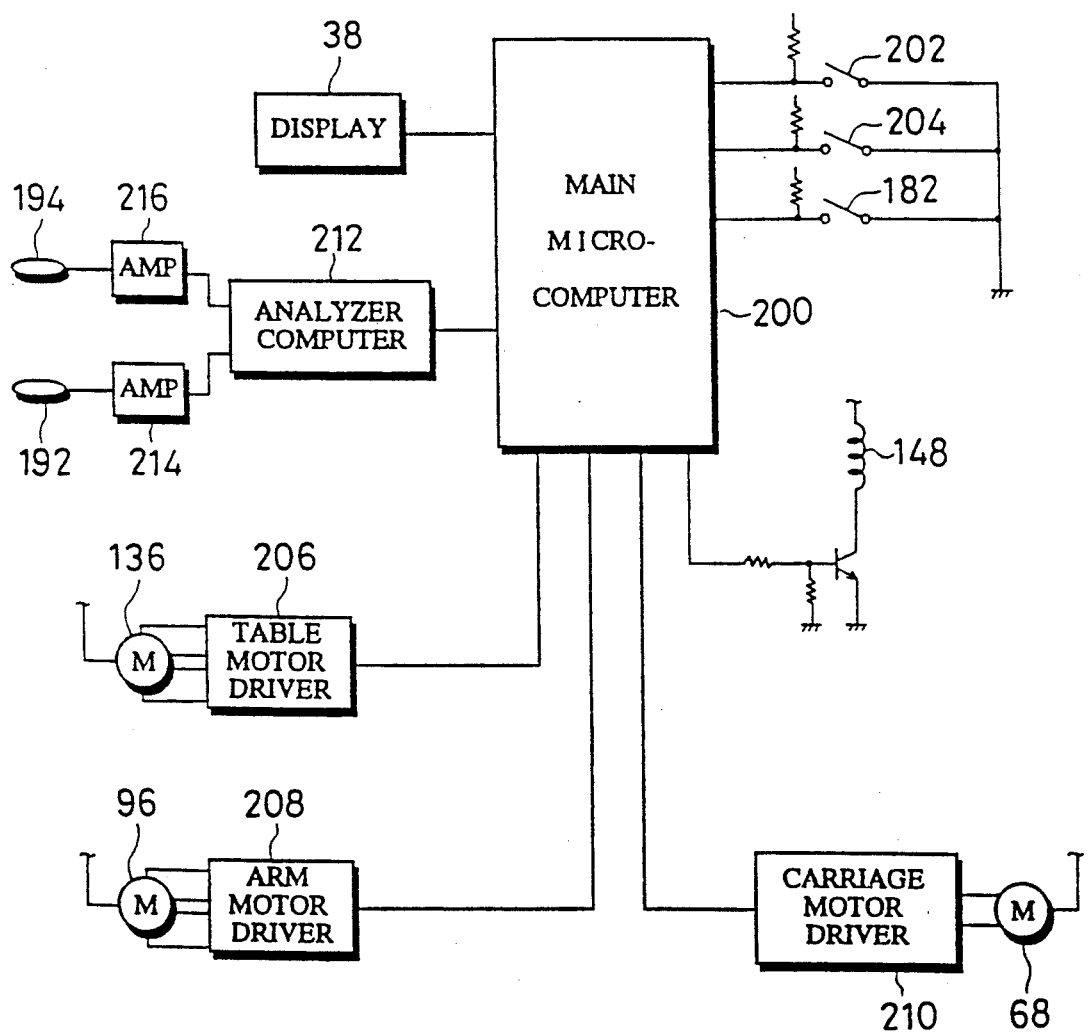
FIG. 22 is a block diagram showing the control circuit as connected to the associated electric components of the toilet system.

FIG. 22 shows a block diagram of the control circuit 36 as connected to the associated electric components of the toilet system. A main microcomputer 200 receives signals from the start button 202 mounted on the lateral housing, the seat switch 204 associated with the toilet seat, and the photosensor 182 acting as a testing sheet detector. The main microcomputer 200 is programmed to control the stepping motor 136 for the movable table 60 through a driver circuit 206, the stepping motor 96 for the slidable arm 50 through another driver circuit 208, the AC motor 68 for the swingable carriage 46 via a further driver circuit 210, and the solenoid actuator 148 for the clamping mechanism. The main microcomputer 200 communicates with another microcomputer 212 programmed for urinalysis. The analyzer microcomputer 212 is adapted to control the LEDs 192 via an amplifier 214 and to receive signals from the photosensors 194 via another amplifier 216. Microcomputers with its associated amplifiers specifically adapted for urinalysis are commercially available from various sources. In the preferred embodiment, the present inventors have used Model HEA-140 marketed by Omron Tateisi Electronics Co., of Kyoto, Japan.

The main computer 200 may be programmed to perform the function as described above with reference to FIGS. 18-20. The operation of the computer 200 will be readily apparent for those skilled in the art when reference is made to the timing charts shown in FIGS. 23A-23G in combination with the flow charts given in FIGS. 24 and 25.

Figure 23:
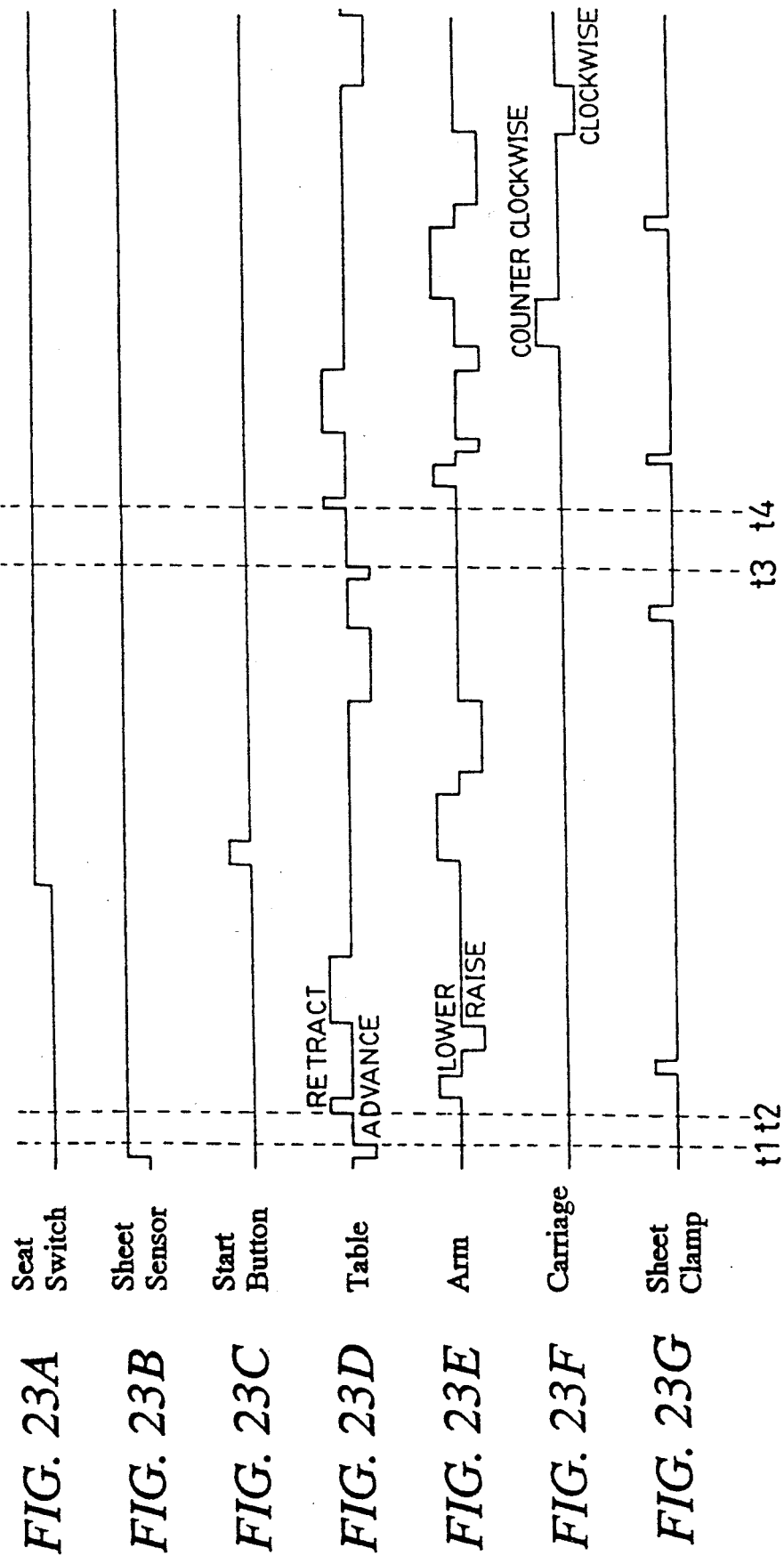
FIG. 23 is a timing chart showing a sequence of various events performed by the toilet system of the invention.
Figure 24:
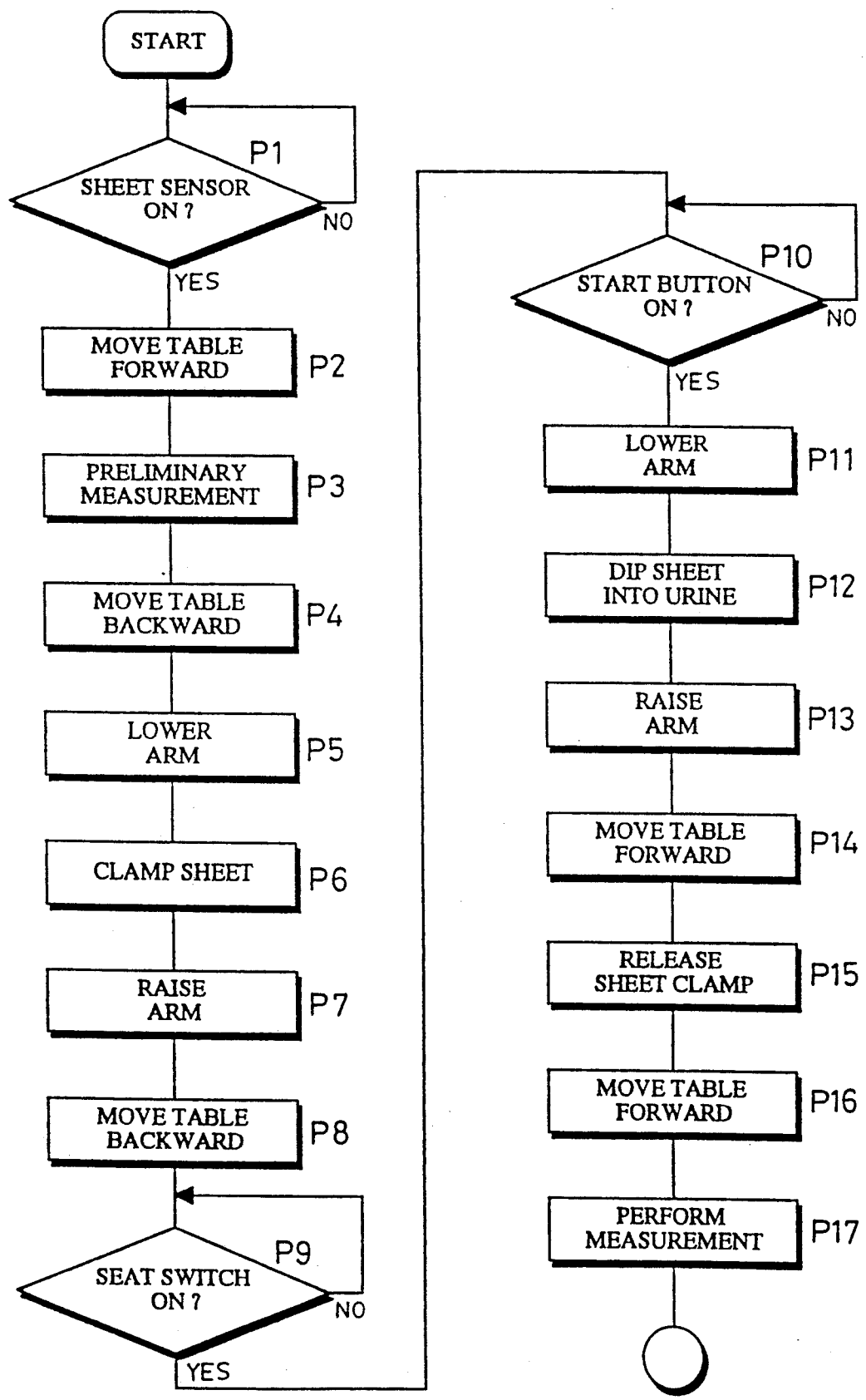
FIGS. 24 and 25 are flow charts showing the events illustrated in the timing chart of FIG. 23.
Figure 25:
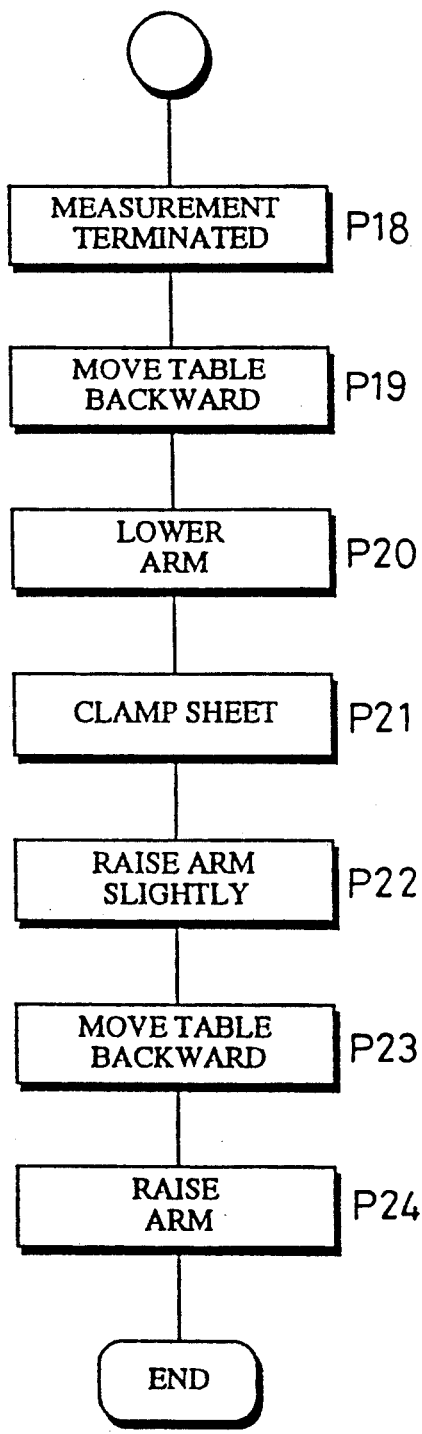

Referring to FIGS. 23A-23G, 24 and 25, when the sheet detecting sensor senses the presence of the testing sheet (FIG. 23B; Point P1 of FIG. 24), the table 60 is moved forward by driving the motor 136 for a predetermined time period and the movement of table is stopped at time t1 (FIG. 23D; Point P2 of FIG. 24). At this point of time, the table is in contact with the stationary head 58. The above-mentioned preliminary measurement is effected during the time interval between time t1 and time t2 (Point P3 of FIG. 24). Then, the table motor 136 is rotated in the reverse direction for a predetermined time period to move the table backward (FIG. 23D; Point P4 of FIG. 24). At the end of table movement, the slidable arm 50 is protracted (FIG. 23E; Point P5 of FIG. 24) and solenoid 148 is energized to clamp the testing sheet (FIG. 23G; Point P6 of FIG. 24). Thereafter, the arm is retracted (FIG. 23E; Point P7 of FIG. 24) and the table is moved backward (FIG. 23D; Point P8 of FIG. 24). As the seat switch is turned on by the user being seated (FIG. 23A; Point P9 of FIG. 24), the system stands by and awaits for the instructions of the user. When the user presses on the start button (FIG. 23C; Point P10 of FIG. 24), the arm is protracted (FIG. 23E; Point P11 of FIG. 24) so that the testing sheet is dipped into the urine pool (Point P12 of FIG. 24). Thereafter, the arm is retracted (FIG. 23E; Point P13 of FIG. 24) and the table is moved forward (FIG. 23D; Point P14 of FIG. 24). Then, the solenoid 148 is energized to release the sheet (FIG. 23G; Point P 15 of FIG. 24) and the table is advanced until it is brought into contact with the stationary head (FIG. 23 D; Point P16 of FIG. 24). Then, the measurement and analysis of the testing sheet is carried out from time point t3 to t4 (Point P17 of FIG. 24).

After measurement (Point P18 of FIG. 25), the table is retracted (FIG. 23D; Point P19 of FIG. 25) and the arm is extended (FIG. 23E; Point P20 of FIG. 25). Then, the solenoid is energized to clamp the used sheet (FIG. 23G; Point P21 of FIG. 25). The arm is then slightly retracted (FIG. 23 E; Point P22 of FIG. 25) and the table is fully moved backward (FIG. 23D; Point P23 of FIG. 25). Then, the arm is fully retracted (FIG. 23E; Point P24 of FIG. 25) whereupon the carriage is swung to the disposal station (FIG. 23F) and the arm is extended (FIG. 23 E). The solenoid is then energized (FIG. 23G) so that the used testing sheet is discarded into the trash box. Finally, the carriage is turned to its initial orientation (FIG. 23F).

Figure 26:
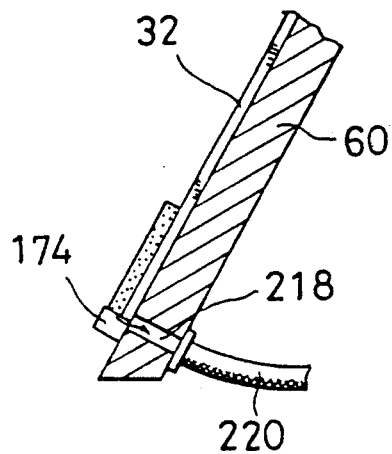
FIG. 26 is a side elevation, partly cut away, showing the lower part of the movable table as provided with a mechanism for the removal of excessive urine.

Various additional features and advantages of the invention will be described below with reference to FIG. 26 and subsequent drawing figures.

Figure 28:
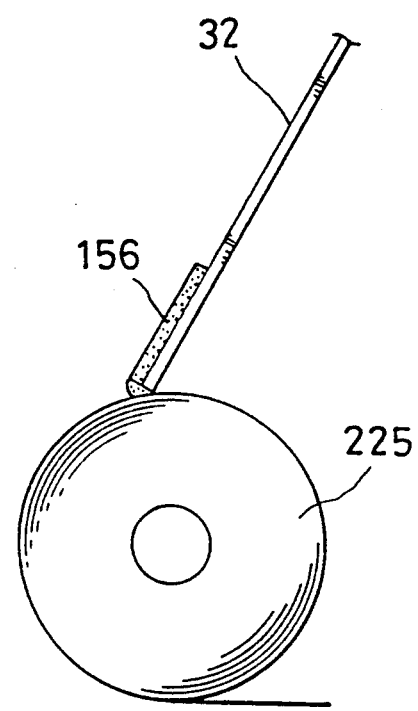
FIGS. 27 and 28 are side elevational views illustrating other forms of the mechanism for removing excessive urine.
Figure 27:
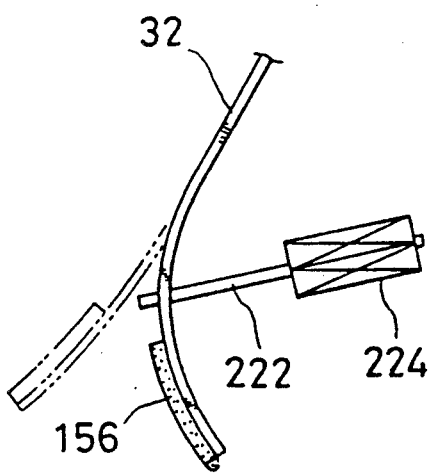

In the urinalysis using the testing sheet, it is important that a proper amount of urine is absorbed by the reagent patches. An excessive amount of urine adhering to the patches would cause undesirably profound reaction, thereby resulting in erroneous or inaccurate analysis. The arrangements illustrated in FIGS. 26-28 is directed to overcome the foregoing problem. Referring to FIG. 26, a plurality of suction ports 218 are provided at the lower part of the movable table 60. These ports 218 also appear in FIG. 13. The suction ports 218 are connected by a conduit 220 to a source of vacuum, which will be described later with reference to FIGS. 29-31. When the testing sheet 32 soaked up with urine is placed on the table 60, a vacuum is applied to the suction ports 218. Any excessive quantity of urine adhering to the reagent patches is sucked into the conduit 220 together with air drawn therein and, thus, only a proper amount of urine is allowed to remain in the absorbent patches. The present inventors have observed that this removal of excessive urine has considerably contributed to enhance the quality of analysis. FIG. 27 illustrates an alternative arrangement for excessive urine removal. There, a hook 222 is provided which is operated by a solenoid actuator 224. As the hook 222 is engaged with the testing sheet and the solenoid 224 actuated, the sheet is flipped so that excessive amount of urine is shaken off. FIG. 28 shows a further alternative arrangement. In this arrangement, a roll 225 of absorbent paper such as toilet paper is used. After the testing sheet is dipped into urine and prior to its placement of the table, the lower edge of the sheet is brought into contact with the paper roll 225 to remove any excessive amount of urine. The portion of the paper roll spoiled by urine may be readily discarded.

Figure 29:
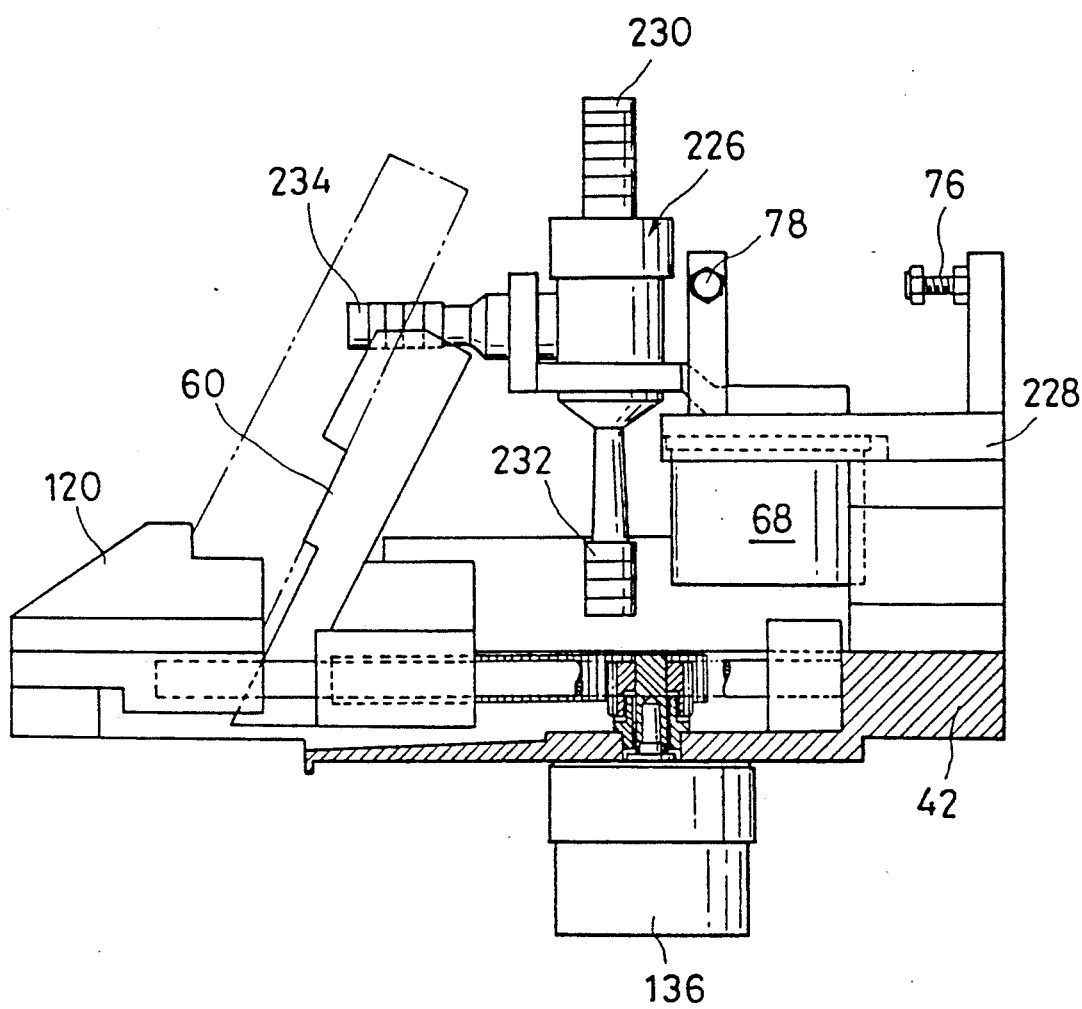
FIG. 29 is a side elevation, partly cut away, showing an eductor pump as mounted to the frame.
Figure 30:
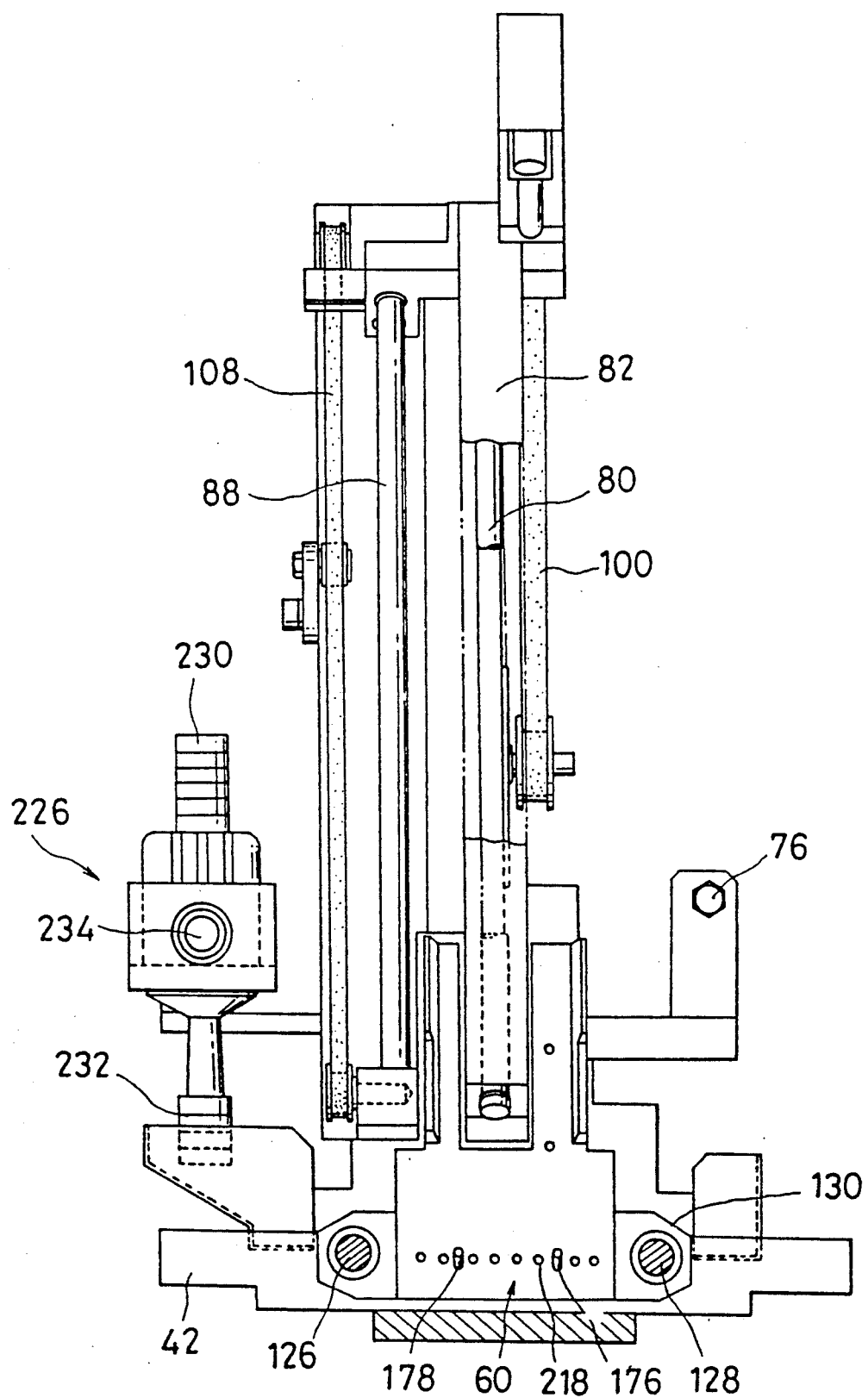
FIG. 30 is a front elevation of the sheet transfer mechanism showing the eductor pump as mounted to the frame.
Figure 31:
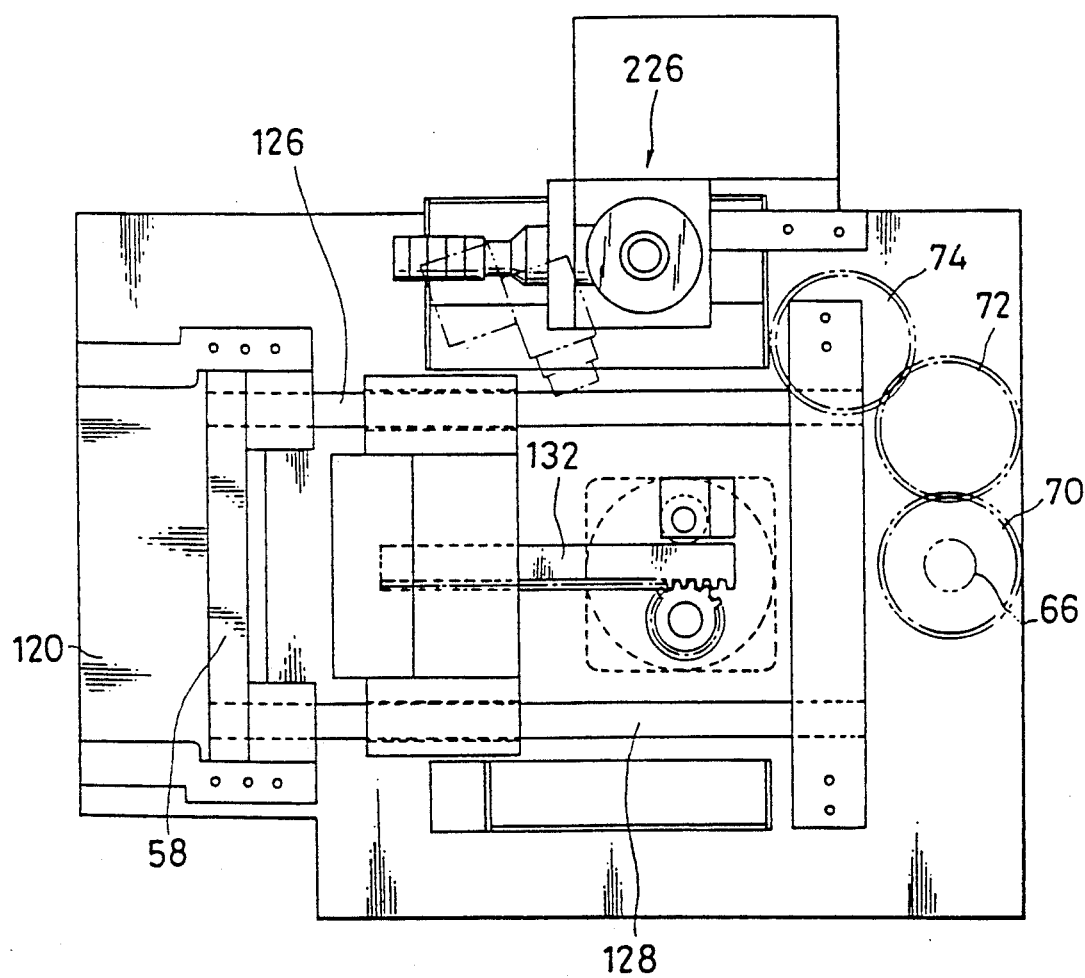
FIG. 31 is a top plan view similar to FIG. 8 but showing the eductor pump as mounted to the frame.

Preferred form of vacuum source suitable for connection to the above described suction conduit 220 is shown in FIGS. 29-31. There is shown an eductor pump 226 which is mounted to that portion 228 of the frame 42 which supports the motor 68 for the swingable carriage 46. The education pump itself is conventional and generates vacuum or negative pressure under the action of fluid flowing through an internal venturi at high speed. The eduction pump 226 shown has an inlet 230, an outlet 232 and a vacuum port 234. In the illustrated arrangement, the inlet 230 is adapted to be connected to a city water supply and the outlet 232 is drained into the toilet bowl 14. The vacuum port 234 is connected to the suction ports 218 (FIG. 26) of the table. Stream of water flowing across the pump 226 draws air at tl vacuum port 234 and, hence, applies vacuum to the suction ports 218 (FIG. 26) of the table. Excessive quantity of urine drawn from the testing sheet is discharged into the toilet bowl together with the used water and is finally flushed away into the sewage system. The use of the eductor pump 226 as a source of vacuum instead of a rotary vacuum pump is advantageous in the urinalysis environment since the rotary pump is readily attacked and damaged by urine. Moreover, since the excessive urine drawn from the testing sheet is finally discharged into the sewage system, a cleaner system is provided.

Figure 32:
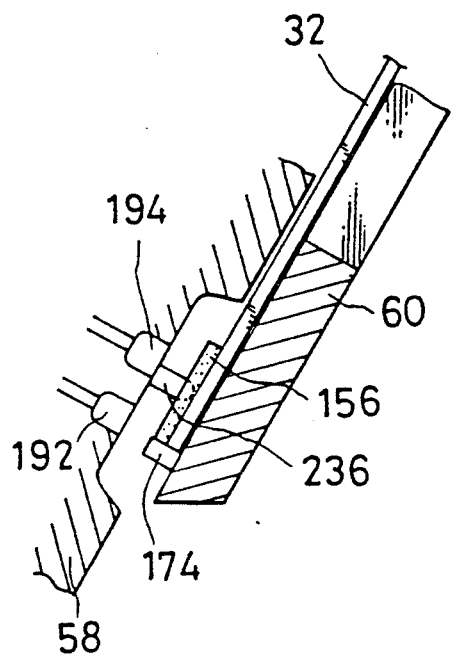
FIG. 32 is a cross-sectional view of part of the stationary head and movable table, showing a form of sheet flattening mechanism.
Figure 33:
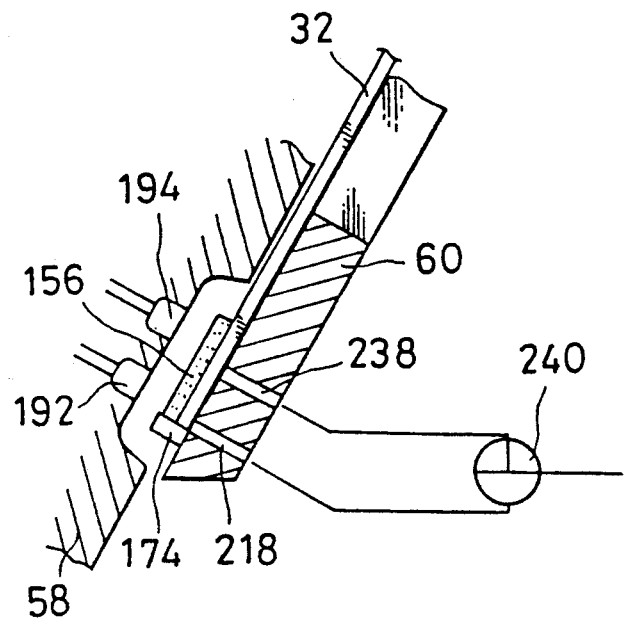
FIG. 33 is a cross-sectional view of part of the stationary head and movable table, showing another form of sheet flattening mechanism.
Figure 34:
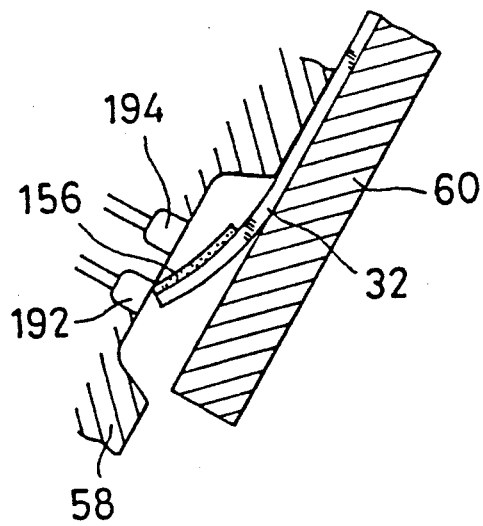
FIG. 34 is a view similar to FIGS. 32 and 33 but showing the sheet as being undesirably deflected.

In order to provide a high quality of analysis, it is also important to have the testing sheet correctly positioned vis-a-vis the LEDs and photosensors during measurement. If there is a bend in the sheet as shown in FIG. 34, the light from the LEDs will not be properly reflected by the sheet so that the photosensors are unable to properly examine the testing sheet. The arrangements shown in FIGS. 32 and 33 are intended to avoid this problem. In the structure shown in FIG. 32, one or more pins 236 are provided on the stationary head 58 and project toward the sheet 32 at points located between adjacent reagent patches. As the table 60 approaches the head 58, the pins 236 urges the testing sheet against the table surface thereby to flatten the sheet. In the arrangement of FIG. 33, one or more suction ports 238 are added to the arrangement shown in FIG. 26. These ports 238 and 218 may be connected to the vacuum port 234 of the eductor pump 228 through a three-way rotary valve 240. When the vacuum is applied to the ports 238 by switching the valve 240, the sheet is attracted by the ports 238 and is flattened against the table.

Figure 35:
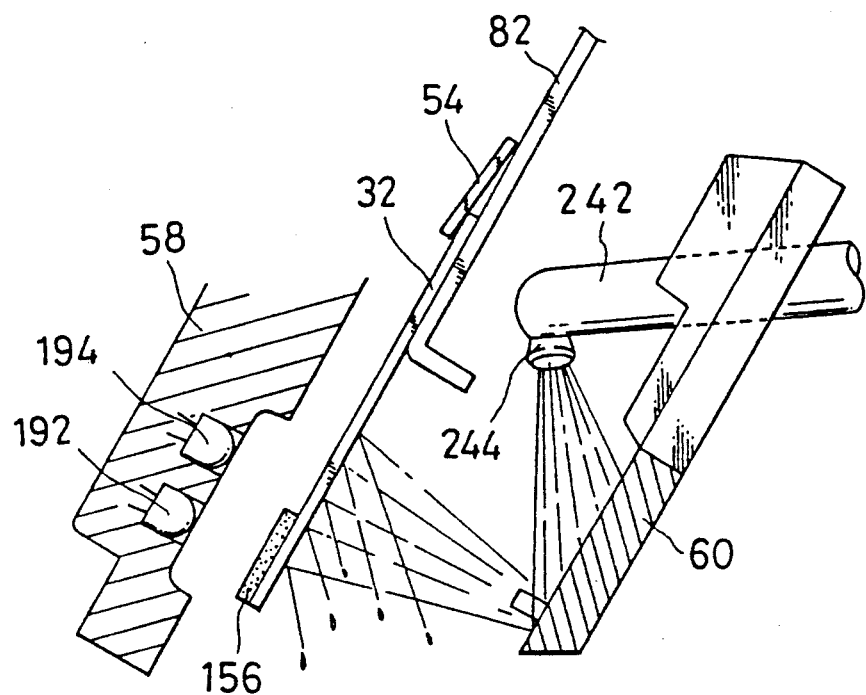
FIG. 35 is a view, partly in cross-section, of part of the stationary head and movable table, showing the table as being flushed in accordance with the preferred sequence of the invention.
Figure 36:
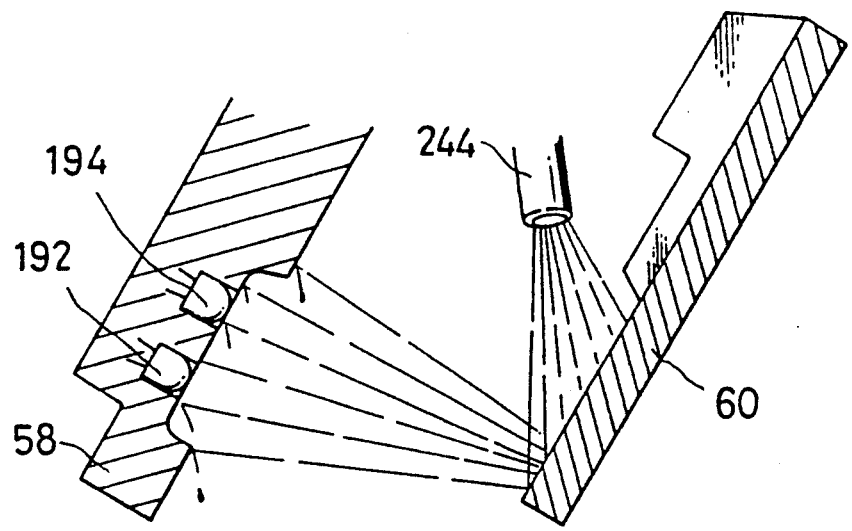
FIG. 36 is a view similar to FIG. 35 but showing undesirable condition of table flushing.

Each time the testing sheet soaked up with urine is mounted on the table 60 for analysis, the table surface 136 will be wetted by urine. To ensure that a fresh testing sheet is not contaminated by residual urine having adhered to the table surface in the preceding analysis, it is desirable to wash and clean the table surface after each analysis. Accordingly, a table flushing arrangement is provided as shown in FIG. 35. A water supply conduit 242 is connected to suitable source of water (not shown) and is provided with a nozzle 244 as shown in FIG. 35. The conduit 242 may arranged laterally of the movable table 60 so as not to interfere with the movement of the table. Alternatively, the conduit 242 may be arranged in such manner as to extend through the central recess 172 (FIG. 13) of the movable table. The nozzle 244 is arranged such that, when the table 60 is fully retracted as shown by the dotted line in FIG. 5, water spray issuing therefrom is directed to the table surface. Flushing of table may be carried out each time urinalysis is completed. It is preferable to perform flushing with the testing sheet positioned in front of the stationary head 58 as shown in FIG. 35. Otherwise, water spray repelled by the table surface would spoil the sensors and LEDs of the head 58 as shown in FIG. 36. With this arrangement, the sensors are protected against and shielded from water spray.

Figure 37:
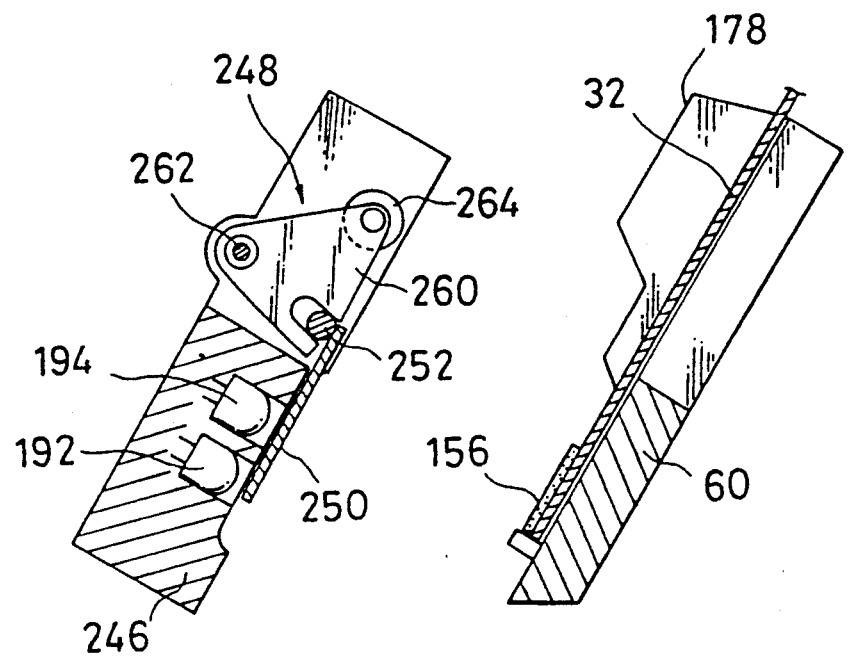
FIGS. 37 and 38 are side elevational views, partly cut away, showing a shutter mechanism.
Figure 38:
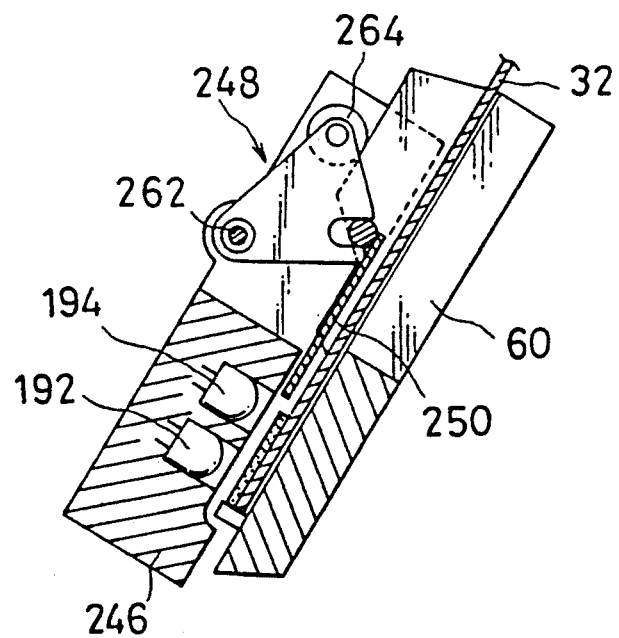
Figure 39:
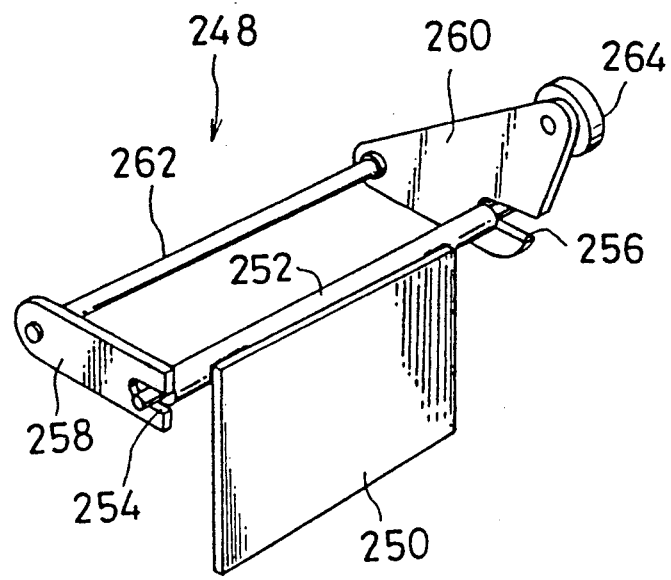
FIG. 39 is a perspective view of the shutter mechanism as shown in FIGS. 37 and 38.

FIGS. 37-39 illustrate another arrangement for shielding the sensors from such undesirable spray. In this embodiment, a stationary head 246, which is similar in function to the head 58 described before, is provided with a shutter mechanism 248 having a shutter blade 250. As best shown in FIG. 39, the blade 250 is joined to a pivot 252 having their ends engaged in slots 254 and 256 formed, respectively, in a pair of lever members 258 and 260. The lever members 258 and 260 are joined together by a pivot 262 which is rotatably supported by the head 246. One of the lever members, say 260, is provided with a roller 264 which is adapted to engage the lateral flange 178 of the table 60. The shutter mechanism 248 also has a counter balance or return spring (not shown) serving to hold the shutter blade 250 parallel to the plane of the head 246 and to normally bias the blade in the closed position as shown. As the movable table 60 is advanced, the roller 264 rides on the flange 178 thereby causing the lever members 260 to swing counterclockwise as viewed in FIGS. 37 and 38, whereby the shutter blade 250 is raised to uncover the LEDs and photosensors as shown in FIG. 38. Measurement of the testing sheet is carried out in this position of the blade. As after measurement the table is moved backward for the purpose of flushing the table surface, the shutter blade 250 is automatically returned to its normally closed position under the action of counter balance or spring as shown in FIG. 37. In this position, table flushing may safely be effected.

Figure 40:
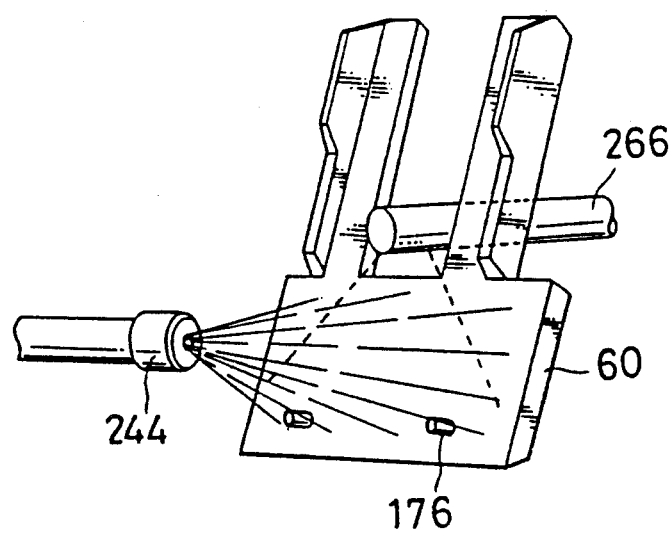
FIGS. 40–42 are perspective views showing various forms of mechanism for removing residual water.
Figure 41:
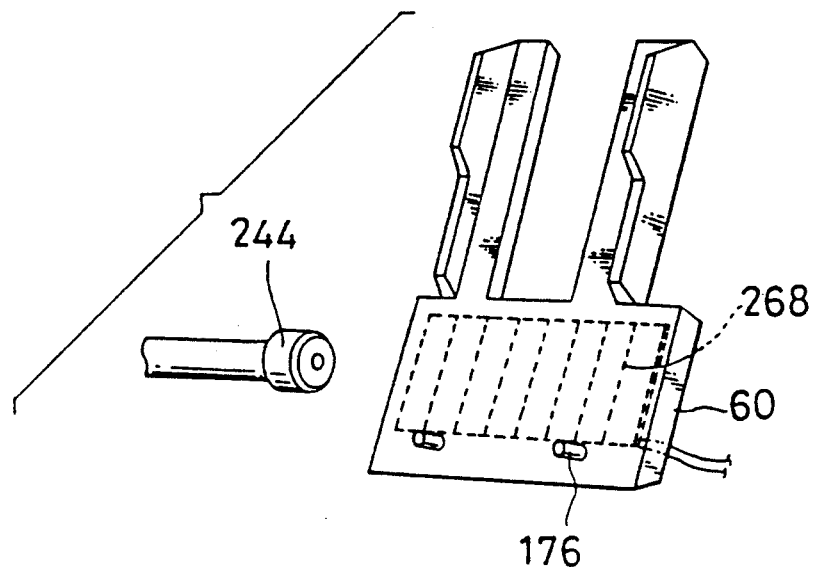
Figure 42:
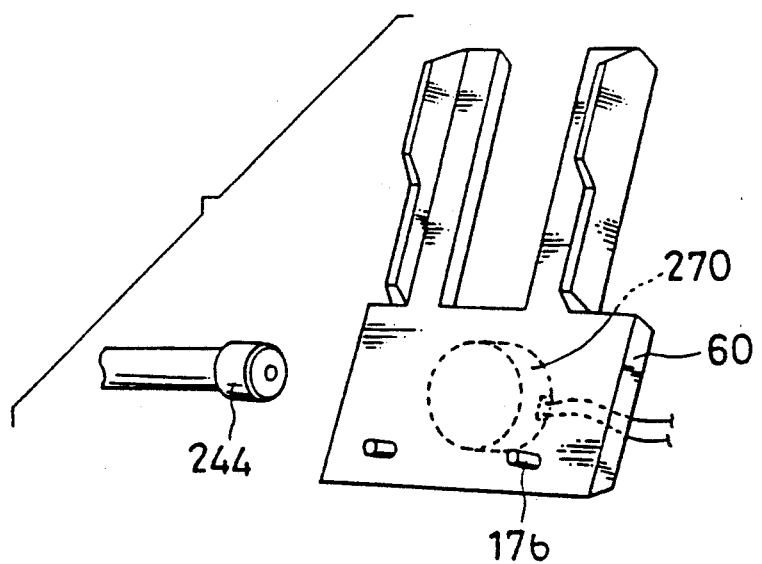

It is preferable that the surface 136 of the table 60 thus flushed with water is dried prior to subsequent measurement. Otherwise, any residual quantity of flushing water adhering to the table surface would come in contact with the testing sheet to thereby dilute urine absorbed in the testing sheet. This will adversely affect the reliability of analysis. Accordingly, the invention provides additional features of removing residual flushing water adhering to the table surface after flushing, as illustrated in FIGS. 40-42. Referring to FIG. 40, an air conduit 266 having a plurality of air nozzles is arranged to extend through the central recess 172 of the movable table 60 and is connected to a source of air under pressure. After flushing of the table surface with water spray from the water nozzle 244, a blow of air may be directed to the table surface through nozzles of the air conduit so as to blow off the residual water. Alternatively, the residual water may be dried by an electric heater 268 embedded in or printed on the table, as illustrated in FIG. 41. Also, an ultrasonic oscillator 270 may be used to purge the residual water as shown in FIG. 42.

Figure 43:
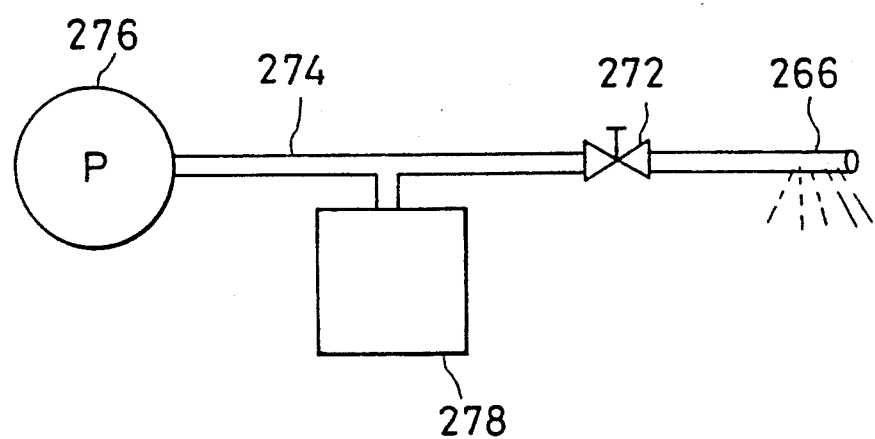
FIG. 43 is a diagrammatic representation of a preferred arrangement for the mechanism for removing residual water.

Preferably, as shown in FIG. 43, the air conduit 266 shown in FIG. 40 is connected to a valve 272 which, in turn, is connected through a conduit 274 to an air compressor 276. An air accumulator 278 is communicated with the conduit 274. With this arrangement, upon opening the valve 272 an abrupt blow of air is released from the nozzles so that the residual water is effectively expelled.

As mentioned in the introductory part of the present specification, the designing requirements for the urine sampling cavity is that it must be made as small as possible to ensure that any quantity of water existing in the sampling cavity be completely displaced and replaced by a flow of fresh urine. As is well known, a toilet stool is made by preparing a green of ceramic forming materials, molding the green into a preform, drying the molded preform, and finally sintering the preform into ceramics. During the course of all these ceramic forming processes, the products undergo substantial change in shape and dimension. Accordingly, it has been the general practice in the industries to permit a tolerance in the order of 10 mm. Such a large tolerance, in combination with the small size of the urine sampling cavity, makes it extremely difficult to correctly and properly dip the testing sheet into the urine pool.

Figure 44:
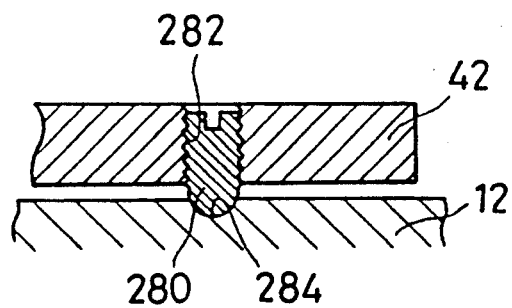
FIG. 44 is a cross-sectional view showing in an enlarged scale the part encircled in FIG. 45.
Figure 45:
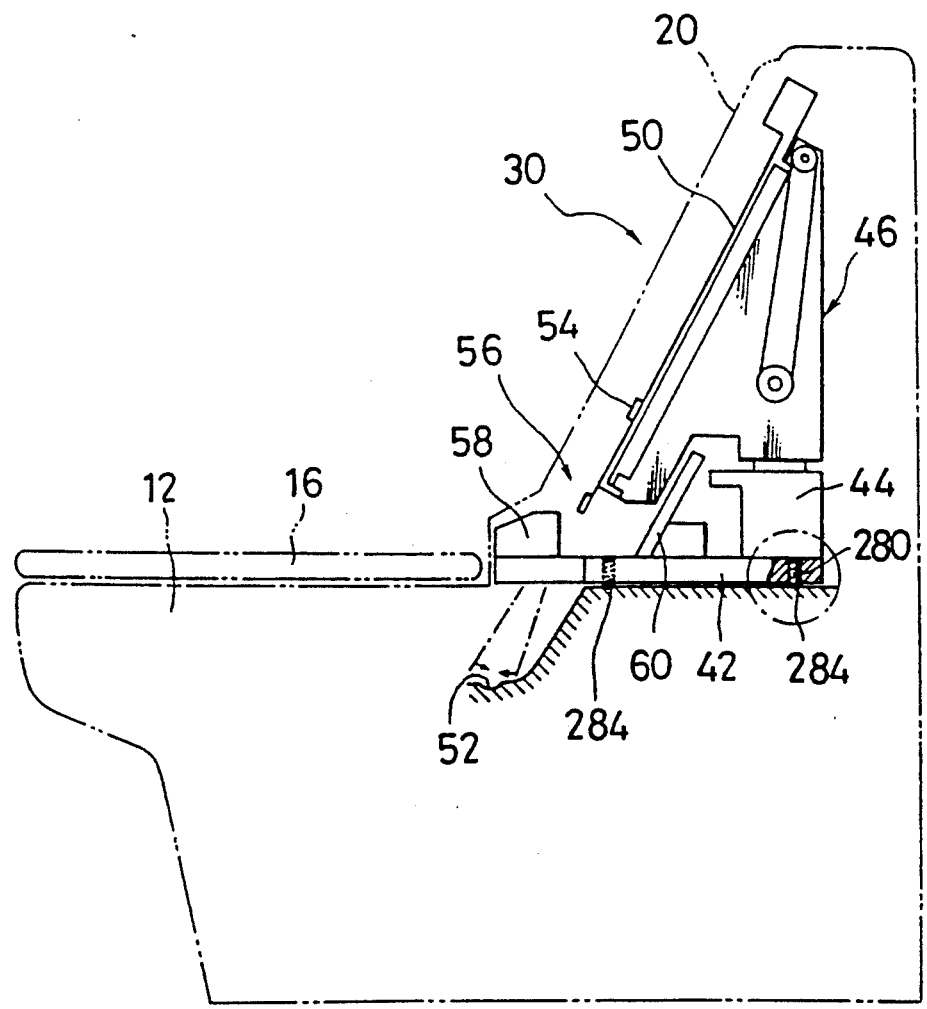
FIG. 45 is a view similar to FIG. 3 but illustrating the sheet transfer mechanism as being adjusted according to the preferred embodiment thereof.
Figure 46:
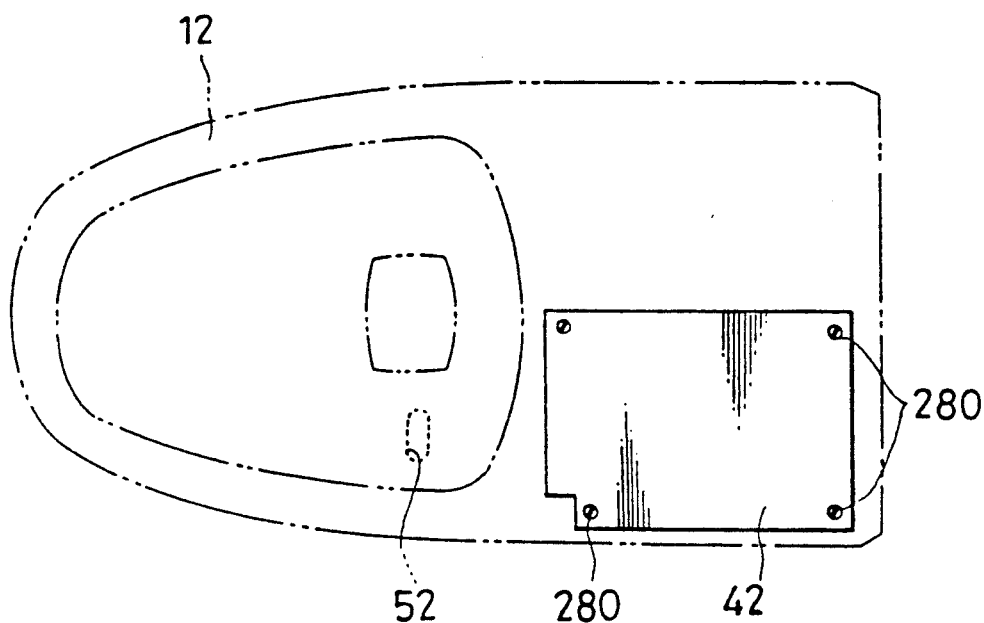
FIG. 46 is a top plan view of the adjustable frame as mounted to the toilet stool.

In view of the foregoing, the toilet system according to the invention may be provided with a simple and effective mech nism for assuring precise alignment of the slidable arm 50 (and, hence, of the testing sheet 32) with respect to the urine sampling cavity 52, as shown in FIGS. 44-46. Referring to these figures, the frame 42 of the sheet transfer mechanism 30 is adjustably supported on the toilet stool 12 by means, for example, of four adjustable screws 280 which are threadingly engaged in corresponding threaded bores 282 in the frame 42. Each screw 280 is preferably engaged in a shallow depression 284 formed on the rear upper surface of the stool 12. By turning the screws 280, the angular position of the arm 50 is adjusted in the longitudinal direction of the toilet system as shown in FIG. 45, as well as in the transverse direction thereof. Thus, with this arrangement, it is possible to precisely align the arm 50 with respect to the urine sampling cavity 52. This, n turn, enables to contact the testing sheet with a proper amount of urine.

Figure 47:
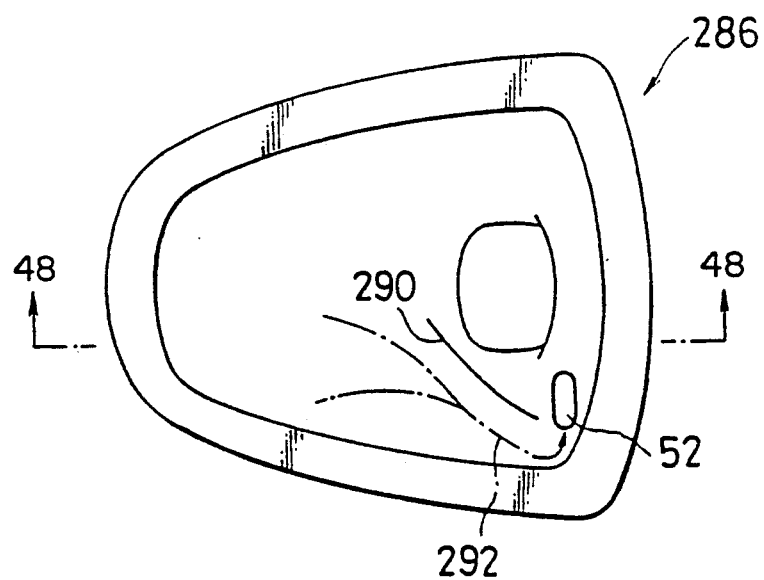
FIG. 47 is a top plan view showing a modified form of the toilet bowl.
Figure 48:
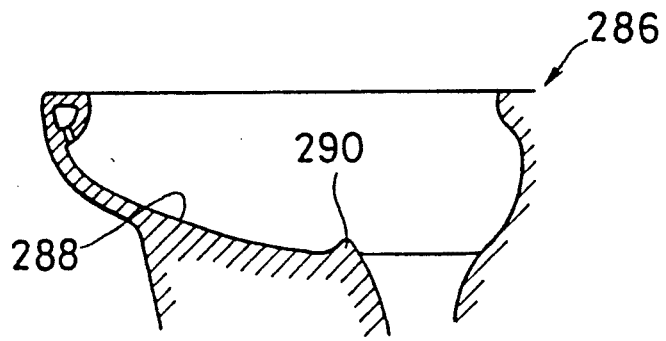
FIG. 48 is a cross-sectional view taken along the line A—A of FIG. 47.
Figure 49:
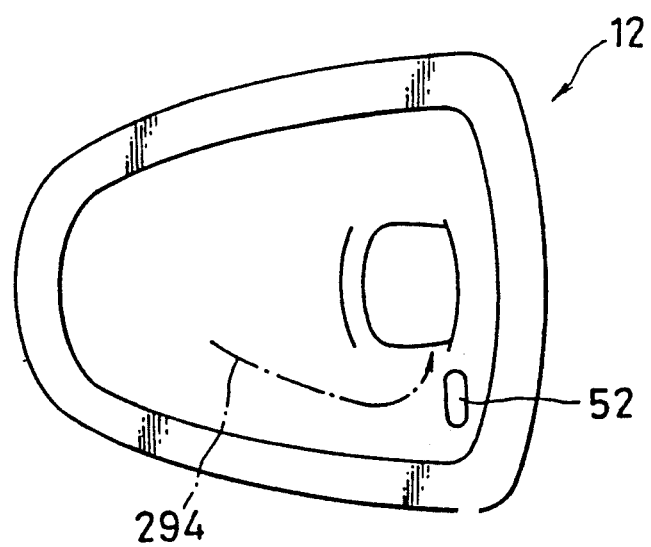
FIG. 49 is a view similar to FIG. 47 but showing the toilet bowl prior to modification.

Referring to FIGS. 47-48, there is shown a preferred modified form of a toilet stool suitable for us in the toilet system according to the invention. The modified toilet stool 286 has a toilet bowl 288 which is designed to direct the flow of urine flowing along the bowl surface toward the urine sampling cavity 52. In the illustrated embodiment, the structure for directing the urine flow comprises a rib 290 that extends from about the central part of the bowl to near the left-hand edge of the sampling cavity 52. Because of the presence of the rib 290, a flow path is formed on the bowl surface as shown by the arrow 292. Therefore, the most part of urine flowing on the frontal part of the bowl surface will be collected by the rib 290 and forcibly directed to the sampling cavity 52. In this manner, water existing in the sampling cavity 52 is replaced 100% by fresh urine. This feature is advantageous in enhancing the reliability of analysis. In contrast, in the absence of such structure, there is a likelihood of the urine flow to short-circuit the sampling cavity 52 as shown by the arrow 294 in FIG. 49.

Figure 50:
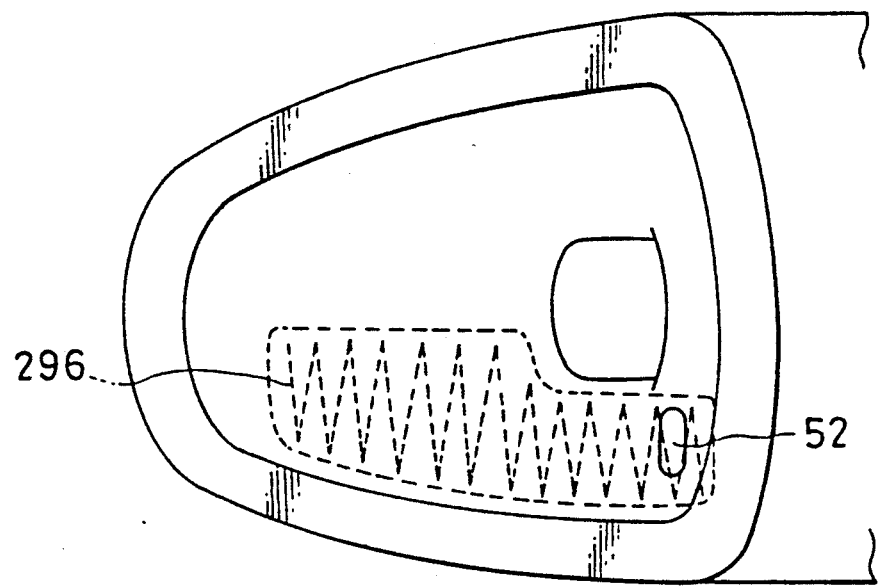
FIGS. 50–52 are views showing a toilet bowl provided with a heater.
Figure 51:
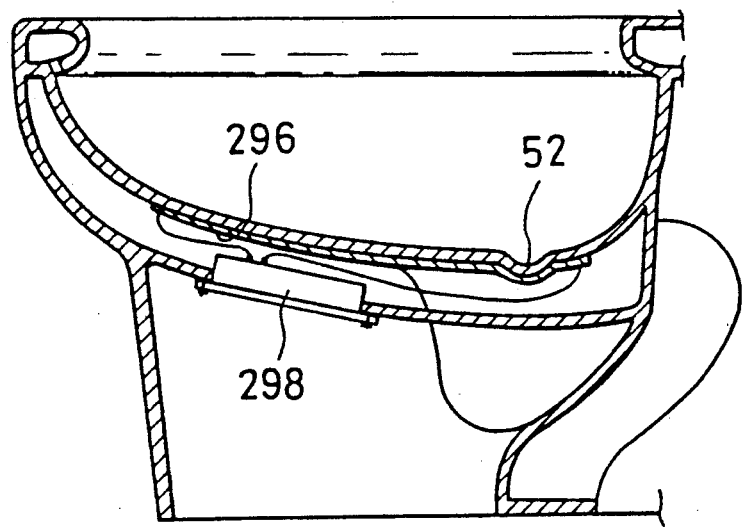
Figure 52:
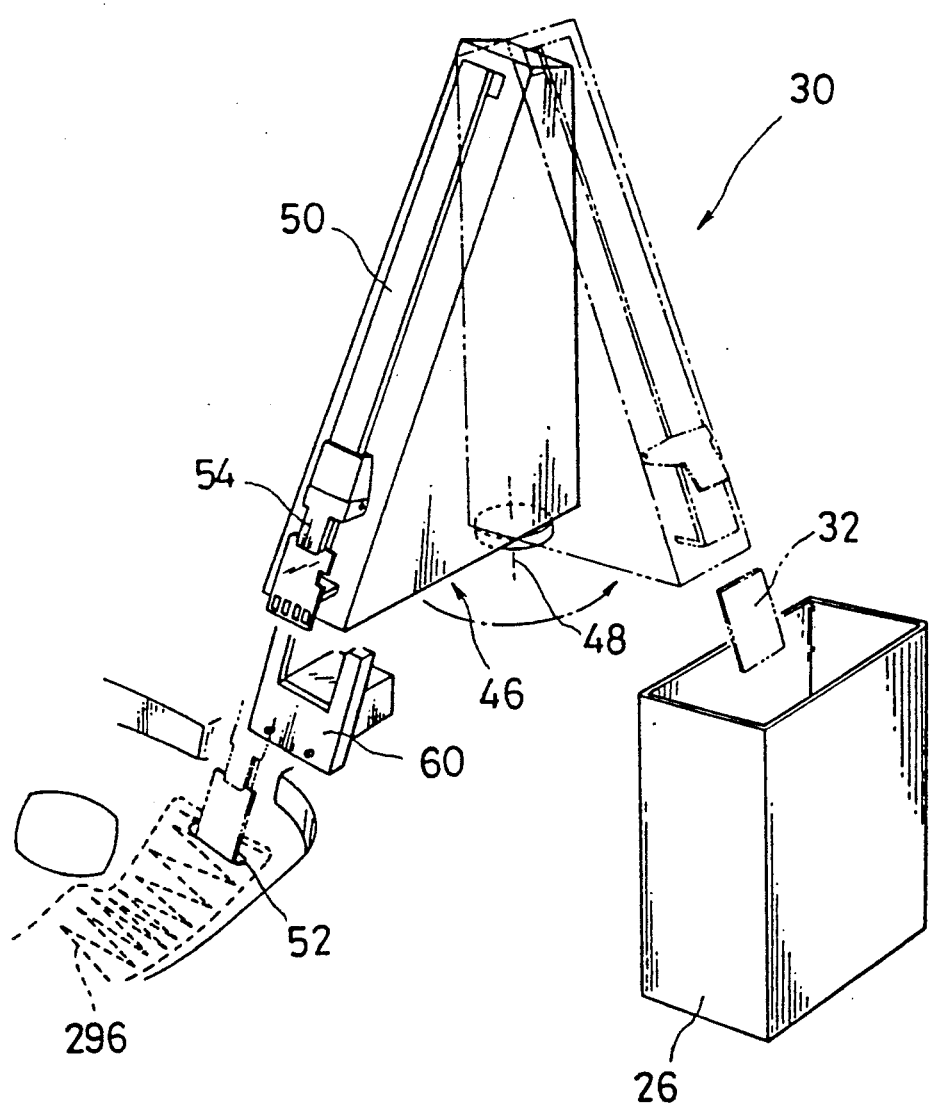
Figure 53:
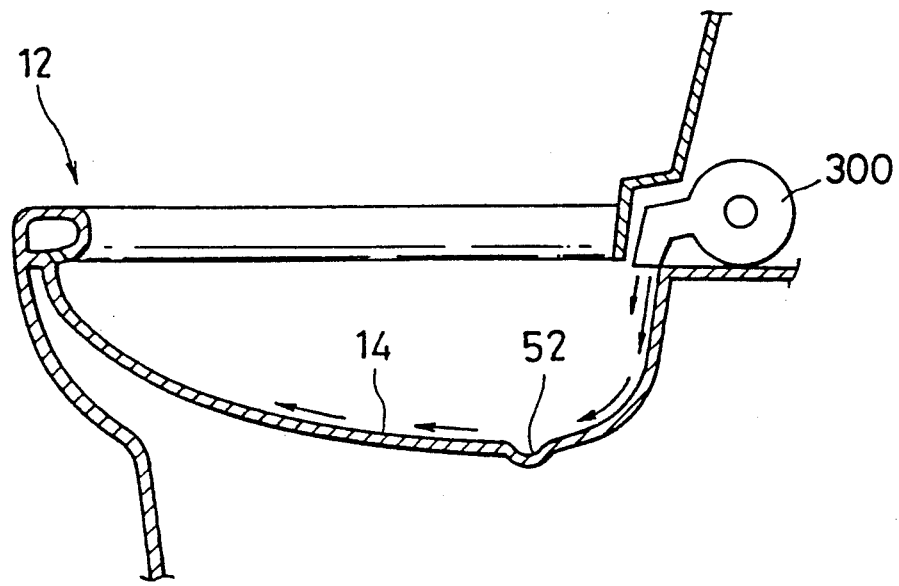
FIG. 53 is a cross-sectional view of a toilet bowl equipped with a blower.

The embodiments shown in FIGS. 50-53 are directed to heating arrangement for the toilet bowl. Referring to FIGS. 50-52, the toilet bowl 14 is provided with an electric heater 296 which is connected to a controller 298. The controller 298 senses the temperature of the bowl and supplies power to the heater 296 as the temperature of the bowl becomes lower than a predetermined value. Thus, the toilet bowl and the urine pool collected in the sampling cavity 52 will be constantly held at a uniform temperature. The advantage of this is that a uniform color reaction of reagents is permitted. FIG. 53 illustrates an alternative embodiment wherein a heater-blower 300 is used. The blower 300 also senses the ambient temperature and feeds heated air into the toilet bowl whenever the temperature is lower than a desired value.

Figure 54:
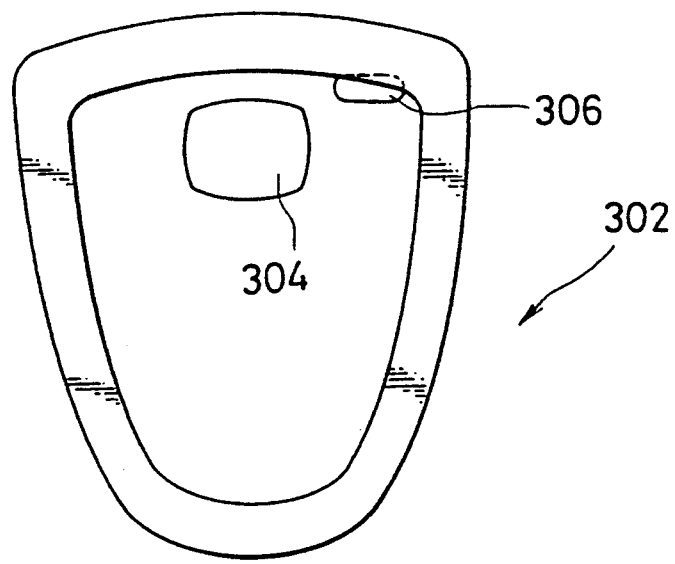
FIG. 54 is a top plan view showing another modified form of the toilet bowl.

FIG. 54 shows another modified form of the toilet stool. The stool 302 has a conventional basin 304. A urine sampling cavity 306 for the purpose of the invention is offset obliquely rearwardly of the basin 304 as shown. This arrangement has the advantage of preventing feces from entering into the urine sampling cavity.

Figure 55:
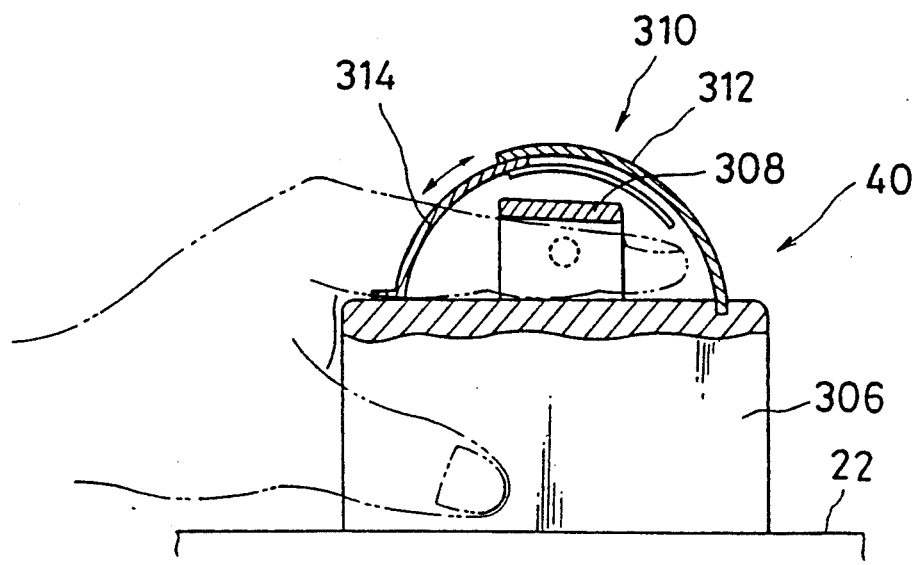
FIG. 55 is a side elevational view, partly in cross-section, showing a digital sphygmomanometer as provided with a cover.
Figure 56:
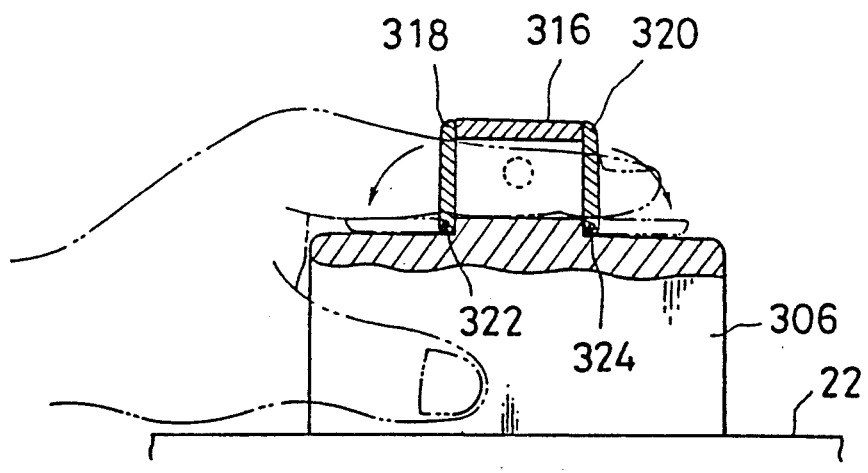
FIG. 56 is a side elevational view, similar to FIG. 55, but showing another form of cover; and, FIG. 57 is a schematic side elevation showing a deodorizing arrangement.

FIG. 55 illustrates in a greater scale the digital sphygmomanometer 40 indicated in FIG. 1. The digital sphygmomanometer itself is well known and, for this reason, will not be described in detail. As shown in FIG. 55, the digital sphygmomanometer 40 includes a main section 306 and a cuff 308. As is well known, while the user inserts its finger into the cuff 308, the main section 306 pumps ar thereto to inflate the cuff. The artery pressure of the user is measured by the principle of digital plethysmogram. According to the invention, the digital sphygmomanometer 40 is provided with a protective cover 310 which is hemispherical in shape. The cover 310 includes a fixed portion 312 and a movable door 314 which is adapted to slide into the fixed portion 312 as shown. The cover 310 is so sized as to allow the user to place its finger into the cuff 308. The provision for the cover 310 is preferable since in a toilet or bathroom environment, water droplets and vapor may degrade the cuff 308. FIG. 56 illustrates an alternative arrangement wherein the cuff 316 is provided with a pair of swingable lids 318 and 320 pivoted at 322 and 324 to the housing of the main section.

Referring again to FIG. 1, there is shown a deodorizing device 326 opening into the housing 24 above the trash box 26. The deodorizing device 326 may comprise an ozone generator or ultraviolet radiator. Thus, any offensive odor arising from the trash box 26 is deodorized and a cleaner environment is provided.

Figure 57:
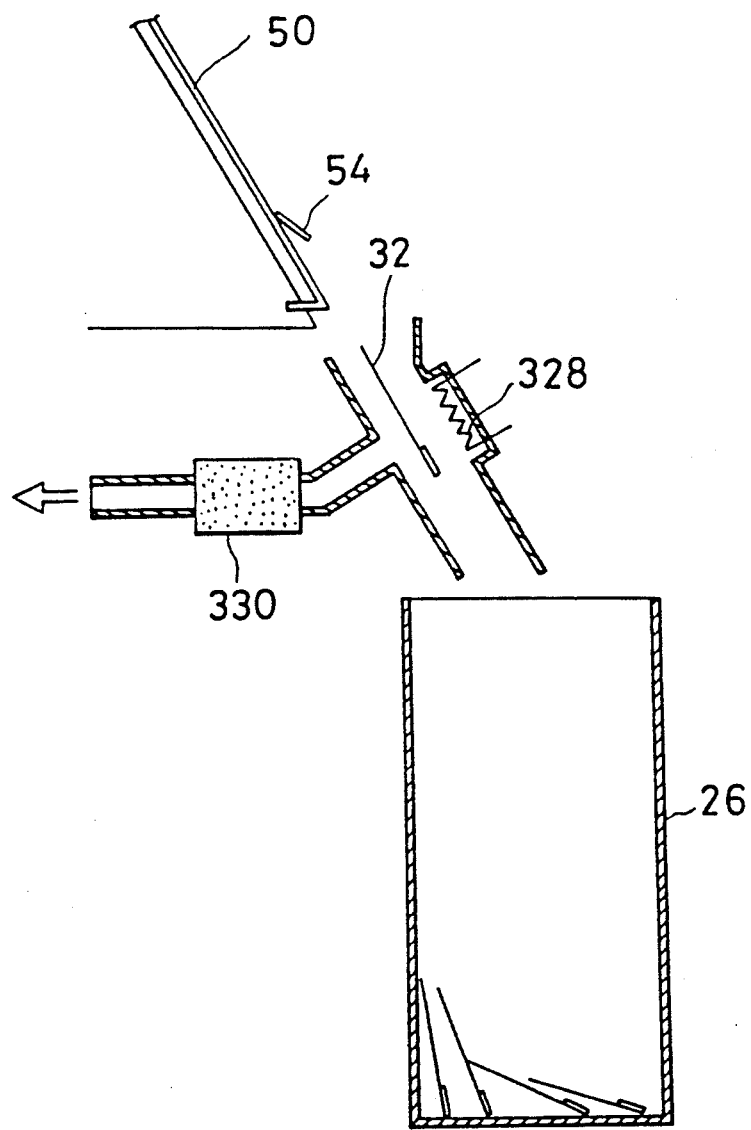

FIG. 57 illustrates another deodorizing arrangement. In this arrangement, the used testing sheet 32 is dried by a heater 328 prior to disposal into the trash 26. The vapor of urine generated by heating of the sheets is drawn through a filter 330 containing activated charcoal or deodorizer.

While the present invention has been described herein with reference to the specific embodiments thereof, it is contemplated that the present invention is not limited thereby and various changes and modifications may be made therein for those skilled in the art without departing from the scope of the invention.

We claim:

1. An apparatus for the assay of biological excrement comprising:
    a base defining an open cavity for receiving biological excrement released from a user of said apparatus seated on said base;
    a frame mounted on said base;
    an excrement analyzer having an analyzer station positioned on said frame, said analyzer being adapted to quantitatively analyze at least one biological substance contained in the excrement, which substance may be of the health condition of the user, by examining at said analyzer station a testing sheet incorporating a reagent which is reactive with said substance; and,
    sheet transfer means supported on said frame for transferring said testing sheet, past said analyzer station, between a first position in which said reagent is allowed to be brought into contact with the excrement in said cavity and a second position which is spaced away from said cavity and in which the used testing sheet is discarded for disposal.

2. An apparatus according to claim 1, wherein said sheet transfer means comprises: an orientable carriage pivoted to said frame for swinging movement about a vertical axis between said first and second positions; and a slidable arm supported by said carriage for translational movement with respect to the carriage along a plane passing through said vertical axis, whereby lowering of said arm allows the reagent to come into contact with the excrement in the cavity, subsequent raising of said arm allows the testing sheet to be moved into said analyzer station for analysis, and swinging of said carriage permits the used testing sheet to be transferred to said cond position for disposal.

3. An apparatus according to claim 2, wherein said sheet transfer means further comprises means mounted on said arm for releasably holding the testing sheet.

4. An apparatus according to claim 1, wherein said analyzer station comprises: a stationary head fixed to said frame and carrying a sensor for detecting the degree of reaction of the reagent occurred by contact thereof with the excrement; and a movable table adapted to support the testing sheet and supported by said frame for horizontal translational movement to and away from said head; said stationary head and movable table being configured to sandwich a part of the testing sheet therebetween when brought into contact with each other.

5. An apparatus according to claim 1, wherein said analyzer station comprises: a stationary head fixed to said frame and carrying a sensor for detecting the degree of reaction of the reagent occurred by contact thereof with the excrement; and a movable table adapted to support the testing sheet and supported by said frame for horizontal transactional movement to and away from said head; said stationary head and movable table being configured to sandwich a part of the testing sheet therebetween and to form a camera when brought into contact with each other, thereby to preclude disturbing radiations external to the sensor from entering therein.

6. An apparatus according to claim 5, wherein said movable table has an inclined surface to enable the testing sheet when placed thereon to slide therealong under the action of the gravity, the lower end of said inclined table surface being provided with a stopper member for locating the sheet in a predetermined position on said surface, said table having a pair of lateral guides to facilitate placement of the testing sheet at said predetermined position of the table surface.

7. An apparatus according to claim 5, further comprising means for fattening the testing sheet against the table surface.

8. An apparatus according to claim 5, further comprising means for removing excessive excrement adhering to said testing sheet.

9. An apparatus according to claim 8, wherein said means for removing excessive excrement includes: a plurality of suction ports opening onto the surface of said movable table at the lower end of the testing sheet; a source of vacuum; and means for connecting said ports to said vacuum source.

10. An apparatus according to claim 9, wherein said vacuum source comprises an eductor pump that draws air under the action of flowing stream of water.

11. An apparatus according to claim 8, wherein said means for removing excessive excrement includes means for flipping the testing sheet to shake off the excessive excrement adhering to the sheet.

12. An apparatus according to claim 8, wherein said means for removing excessive excrement includes an absorbent material and wherein the portion of the testing sheet carrying the reagent is contacted with said absorbent material after it has been contacted with the excrement and before it is brought to said analyzer station.

13. An apparatus according to claim 5, further comprising means for flushing the surface of said movable table after said examination of the testing sheet.

14. An apparatus according to claim 13, wherein flushing of the table surface is carried out with the testing sheet positioned in front of said stationary head so that the testing sheet shields said sensor on said head from flushing water.

15. An apparatus according to claim 13, further comprising automatic shutter means for shielding said sensor on said stationary head from flushing water while flushing of the table surface is carried out.

16. An apparatus according to claim 13, further comprising means for removing residual flushing water adhering to said table surface after flushing.

17. An apparatus according to claim 16, wherein said means for means for removing residual flushing water includes means for supplying a blow of air onto said surface.

18. An apparatus according to claim 17, wherein said means for supplying a blow of air includes: an air nozzle directed toward said table surface; an air compressor; a conduit connecting said air nozzle and said air compressor; an accumulator for air under pressure in communication with said conduit; and a valve positioned in said conduit between said nozzle and said accumulator, whereby opening of said valve causes an abrupt blow of air under pressure.

19. An apparatus according to claim 16, wherein said means for removing residual flushing water includes a heater mounted to said movable table.

20. An apparatus according to claim 16, wherein said means for removing residual flushing water includes an ultrasonic oscillator.

21. An apparatus according to claim 1, wherein said sheet transfer means comprises; an orientable carriage pivoted to said frame for swinging movement about a vertical axis between said first and second positions, a slidable arm supported by said carriage for translational movement with respect to the carriage along a plane passing through said vertical axis, and a clamping member mounted on said arm for releasably holding the testing sheet, wherein said analyzer station comprises; a stationary head fixed to said frame and carrying a sensor for detecting the degree of reaction of the reagent occurred by contact thereof with the excrement, and a movable table adapted to support the testing sheet and supported by said frame for horizontal translational movement to and away from said head, said movable table having an inclined surface to enable the testing sheet when placed thereon to slide therealong under the action of the gravity, the lower end of said inclined table surface being provided with a stopper member for locating the sheet in a predetermined position on said surface, and wherein said sheet transfer means is operable in such a manner that sad testing sheet clamped by said clamping member s first brought into contact with the excrement in the cavity and is then lifted above said analyzer station and that said clamping member is then released at such a point of time when said movable table has been moved toward said stationary head forwardly enough to locate said stopper member ahead of the lower end of the testing sheet, thereby to permit the released testing sheet to fall upon and slide along said inclined surface of the movable table to arrive at said predetermined position.

22. An apparatus according to claim 21, wherein said sheet transfer means is operable in such manner that, when after analysis the testing sheet placed on the inclined surface of the movable table is to be transferred for disposal, said clamping member first clamps the testing sheet a ; the slidable arm is then raised upwards to disengage the lower end of the testing sheet away from said stopper member, said movable table being thereafter moved backward.

23. An apparatus according to claim 1, wherein said sheet transfer means is operable in such a manner that it completes any actions thereof up to the step of contacting of the testing paper with the excrement and then stands by until further instructions of the operator.

24. An apparatus according to claim 1, wherein, for the assay of urine, said base is made in the form of a toilet stool having a toilet bowl, said cavity being formed on the surface of the toilet bowl above the normal level of water in said bowl for sampling a quantity of urine flowing along the bowl surface.

25. An apparatus according to claim 24 wherein said frame is angularly adjustably mounted with respect to said toilet stool to ensure that the testing sheet held in said first position by said transfer means is aligned with said urine sampling cavity.

26. An apparatus according to claim 24, further comprising means for defining a flow path on the surface of said bowl for directing the flow of urine toward said sampling cavity.

27. An apparatus according to claim 24, further comprising heater means for heating the flow of urine flowing along the bowl surface.

28. An apparatus according to claim 24, wherein said urine sampling cavity is offset rearwardly with respect to a basin of the toilet bowl.

29. An apparatus according to claim 1, wherein said apparatus further comprises a digital sphygmomanometer mounted with respect to said base, said sphygmomanometer having a cuff, and wherein said cuff is protected by a cover.

30. An apparatus according to claim 1, further comprising a trash box for disposal of used testing sheets and means for removing offensive odor arising therefrom.

31. A toilet system with urine assay function comprising:
a toilet stool having a toilet bowl and a urine-sampling cavity open at its top, said sampling cavity being in open flow communication with the upper surface of said bowl and located above the normal level of water in said bowl for sampling a small quantity of urine flowing along the surface of the bowl;
a toilet flushing device;
a frame mounted on said toilet stool substantially at the rear part thereof;
a swingable carriage pivoted to said frame for swinging movement about a vertical axis between a first position in which said carriage is oriented toward said sampling cavity and a second position in which said carriage is oriented to a lateral side of the stool;
a movable arm supported by said carriage for sliding movement with respect to the carriage along a plane passing through said vertical pivot axis, the lower end of said arm being adapted to releasably hold a testing sheet carrying a reagent which is reactive with a biological substance contained in the sampled quantity of urine; and,
an analyzer having an analyzer station mounted to said frame, said analyzer being capable of quantitatively analyzing said biological substance to indicate the health condition of the user of said apparatus.

32. A toilet system according to claim 31, wherein said frame is angularly adjustably mounted with respect to said toilet stool to ensure that the movable arm is aligned with said urine sampling cavity when said carriage is in its first position.

33. A toilet system according to claim 31, wherein adjustable abutment means engageable with said carriage is provided on said frame for adjustably limiting the swinging movement of the carriage between said first and second positions.

34. A toilet system according to claim 31, wherein said toilet bowl is provided with means for directing the flow of urine flowing along the bowl surface toward said sampling cavity for 100% replacement of existing water with a fresh quantity of urine.

35. A toilet system according to claim 31, wherein said movable arm is provided at the lower part thereof with means for releasably clamping the testing sheet.

36. A toilet system according to claim 31, wherein said analyzer station comprises: a stationary head fixed to said frame and carrying a sensor for detecting the degree of reaction of the reagent occurred by contact thereof with the sampled urine; and a movable table adapted to support the testing sheet and supported by said frame for horizontal translational movement to and away from said head; said stationary head and movable table being configured to sandwich a part of the testing sheet therebetween when brought into contact with each other.

37. A toilet system according to claim 31, wherein said analyzer station comprises: a stationary head fixed to said frame and carrying a sensor for detecting the degree of reaction of the reagent occurred by contact thereof with urine; and a movable table adapted to support the testing sheet and supported by said frame for horizontal translational movement to and away from said head; said stationary head and movable table being configured to sandwich a part of the testing sheet therebetween and to form a camera when brought into contact with each other, thereby to preclude disturbing radiations external to the sensor from entering therein.

38. A toilet system according to claim 36, wherein said movable table has an inclined surface to enable the testing sheet when placed thereon to slide therealong under the action of the gravity, the lower end of said inclined table surface being provided with a stopper member for locating the sheet in a predetermined position on said surface, said table having a pair of lateral guides to facilitate placement of the testing sheet at said predetermined position of the table surface.

39. A toilet system according to claim 36, further comprising means for removing excessive urine adhering to said testing sheet.

40. A toilet system according to claim 39, wherein said means for removing excessive urine includes: a plurality of suction ports opening onto the surface of said movable table at the lower end of the testing sheet; an eductor pump which draws air under the action of water stream flowing therethrough; and means for connecting said ports to said eductor pump.

41. A toilet system according to claim 36, further comprising means for flushing the surface of said movable table with water after analysis.

42. A toilet system according to claim 41, wherein flushing of the table surface is carried out with the testing sheet positioned in front of said stationary head so that the testing sheet shields said sensor on said head from flushing water.

43. A toilet system according to claim 41, further comprising means for removing residual flushing water adhering to said table surface after flushing.

44. A toilet system according to claim 31, wherein a trash box for disposal of used testing sheets is provided at a lateral side of the stool at said second position of the swingable carriage.

45. A toilet system according to claim 44, further comprising means for removing offensive odor arising from said trash.

46. A toilet system with urinalysis function for the self-diagnosis of the health condition comprising:
- a toilet stool having a toilet bowl and a urine-sampling cavity open at its top, said sampling cavity being in open flow communication with the upper surface of said bowl and located above the normal level of water in said bowl for sampling a small quantity of urine flowing along the surface of the bowl;
- a toilet flushing device;
- a frame mounted on said toilet stool substantially at the rear part thereof;
- a swingable carriage pivoted to said frame for swinging movement about a vertical axis between a first position in which said carriage is oriented toward said sampling cavity and a second position in which said carriage is oriented to a lateral side of the stool;
- a movable arm supported by said carriage for sliding movement with respect to the carriage along a plane passing through said vertical pivot axis, the lower part of said arm having a clamping member for releasably clamping a testing sheet carrying a reagent which is reactive with a biological substance contained in urine; and,
- an analyzer having an analyzer station mounted to said frame, said analyzer being capable of quantitatively analyzing said biological substance and being adapted to display the results of analysis to indicate the health condition.

47. A sheet handling device, for use in a toilet system with urine assay function, for the handling of a testing sheet adapted to detect a urinary substance indicative of the health condition of human, said toilet system having a urine sampling station for the sampling of a quantity of urine, said device comprising:
- a frame adapted to be affixed to said toilet system;
- a swingable carriage pivoted to said frame for swinging movement about a vertical axis between a first position in which said carriage is oriented toward said urine sampling station and a second position in which said carriage is oriented to a lateral side of the toilet system; and,
- a slidable arm supported by said carriage for sliding movement with respect to the carriage along a plane passing through said vertical pivot axis, the lower end of said arm having means for releasably holding said testing sheet.

48. A sheet handling device according to claim 47, wherein said device further comprises: a stationary head fixed to said frame and adapted to support a sensor for analyzing the testing sheet; and a movable table supported by said frame for horizontal translational movement with respect to said stationary head; said stationary head and movable table forming a dark room for the sensor when they are brought into contact with each other with the testing sheet sandwiched therebetween.

49. A sheet handling device according to claim 48, wherein said movable table has an inclined surface to permit the testing sheet placed thereon to slide therealong under the action of the gravity, the lower end of said inclined table surface being provided with a stopper member for locating the sheet in a predetermined position on said inclined table surface.

50. A sheet handling device according to claim 49, wherein said inclined table is provided with a pair of lateral guides to facilitate placement of the testing sheet at said predetermined position of the table surface.

51. A sheet handling device according to claim 49, wherein said slidable arm is inclined at an angle equal to the inclination of the surface of said movable table.

* * * * *